(12) United States Patent
McFall et al.

(10) Patent No.: US 7,056,404 B2
(45) Date of Patent: Jun. 6, 2006

(54) METHODS OF BONDING MATERIALS, ESPECIALLY MATERIALS USED IN ABSORBENT ARTICLES

(75) Inventors: Ronald Ray McFall, West Chester, OH (US); Dennis Allen DeHaan, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 346 days.

(21) Appl. No.: 10/456,288

(22) Filed: Jun. 6, 2003

(65) Prior Publication Data

US 2005/0087292 A1    Apr. 28, 2005

Related U.S. Application Data

(63) Continuation-in-part of application No. 09/555,356, filed as application No. PCT/US98/25222 on Nov. 25, 1998, now abandoned.

(51) Int. Cl.
*B32B 31/00*    (2006.01)

(52) U.S. Cl. .................. 156/209; 156/290; 156/308.2; 156/308.4

(58) Field of Classification Search ............... 156/209, 156/308.2, 308.4, 290
See application file for complete search history.

(56) References Cited

U.S. PATENT DOCUMENTS 4,075,382 A    2/1978    Chapman
4,196,562 A    4/1980    Hirschman
4,240,416 A    12/1980   Boich
4,473,611 A    9/1984    Haq
4,854,984 A    8/1989    Ball
5,269,983 A    12/1993   Schulz
5,451,452 A    9/1995    Phan
5,928,452 A    7/1999    McFall
6,173,496 B1   1/2001    Makoui
6,183,587 B1   2/2001    McFall
6,475,346 B1*  11/2002   Lefebvre Du Grosriez . 156/209

FOREIGN PATENT DOCUMENTS

EP    0 374 910 B1       6/1990
EP    0 374 910 B1       7/1993
EP    0 622 064 A2       11/1994
WO    WO 95/13774 A1     5/1995
WO    WO 96/21682 A1     7/1996
WO    WO-99/26769 A2 *   6/1999
WO    WO 02/070243       9/2002

OTHER PUBLICATIONS

PCT International Search Report dated Jun. 1, 1999.
PCT International Search Report dated Oct. 29, 2004.

* cited by examiner

*Primary Examiner*—Jeff H. Aftergut
(74) *Attorney, Agent, or Firm*—James E. Oehlenschlager; Michael S. Kolodesh; David M. Weirich

(57) ABSTRACT

Methods of and apparatus for bonding and/or embossing of materials, especially materials used in the manufacture of hygienic articles, including, but not limited, to absorbent articles such as feminine hygiene articles, disposable diapers, incontinence devices, wipes, and the like.

8 Claims, 11 Drawing Sheets

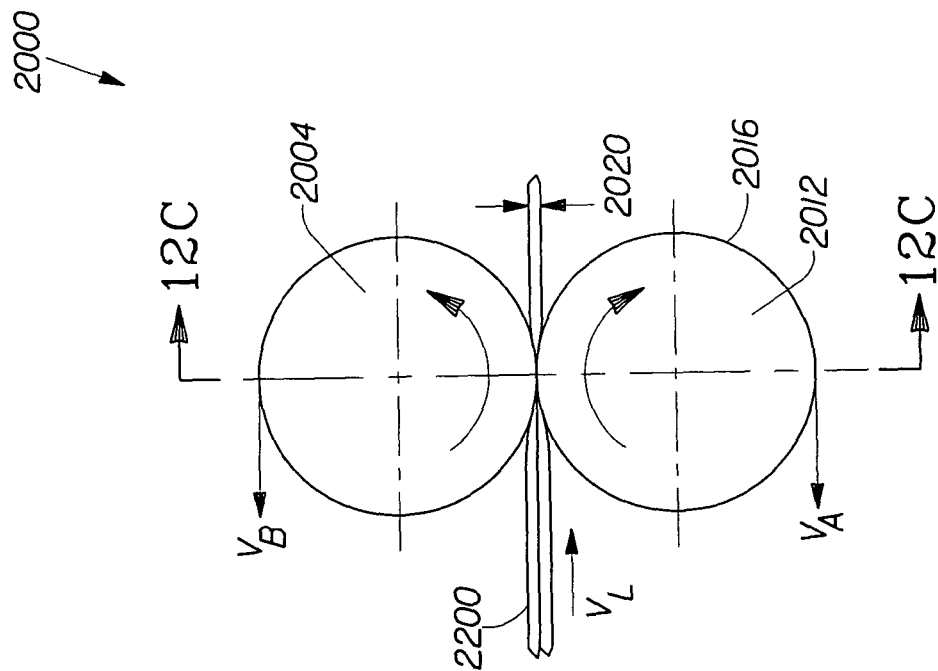
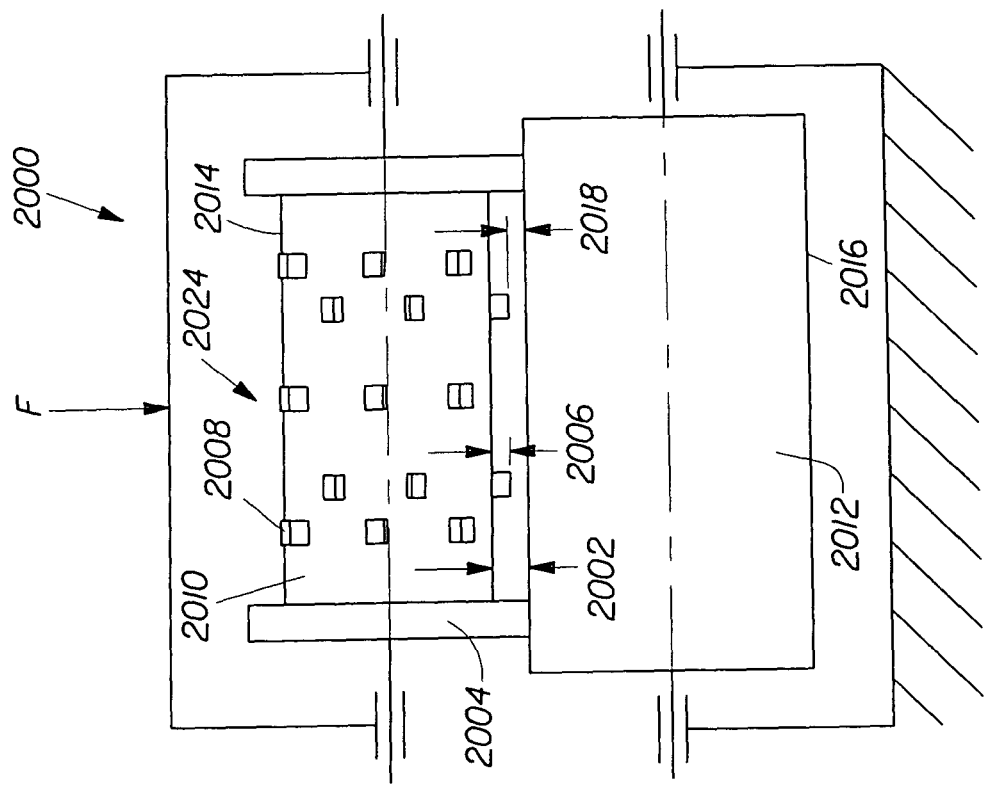
Fig. 12A
Fig. 12B

METHODS OF BONDING MATERIALS, ESPECIALLY MATERIALS USED IN ABSORBENT ARTICLES

CROSS REFERENCE TO RELATED APPLICATIONS

This application is a continuation-in-part of prior U.S. application Ser. No. 09/555,356, filed on Oct. 13, 2000, now abandoned, which was a national stage 371application of international application No. PCT/US98/25222, filed Nov. 25, 1998.

FIELD OF THE INVENTION

The present invention relates generally to methods of bonding materials for use in absorbent articles, although the techniques described herein may be used to bond materials used in other types of articles. In preferred embodiments, the present invention relates to methods which is used in the manufacture of absorbent articles such as sanitary napkins, pantiliners, tampons, absorbent interlabial devices, diapers, incontinence devices, and the like.

BACKGROUND OF THE INVENTION

Absorbent articles such as sanitary napkins, pantiliners, tampons, absorbent interlabial devices, disposable diapers, incontinence products, and bandages are designed to absorb and retain liquid and other discharges from the human body and to prevent body and clothing soiling.

In the manufacture of absorbent articles, it is generally necessary to bond the components that will form the absorbent article together in order to form the finished product. Typical methods for bonding such material include adhesives, heat and/or pressure, and ultrasonics.

Some materials, however, cannot be bonded by these typical bonding techniques because of their structural integrity or composition. One such type of material are absorbent foam materials made from high internal phase emulsions (or "HIPE" foams) such as those described in U.S. Pat. No. 5,260,345 issued to DesMarais, et al. on Nov. 9, 1993; U.S. Pat. No. 5,268,224 issued to DesMarais, et al. on Dec. 7, 1993; and U.S. Pat. No. 5,387,207 issued to Dyer, et al. on Feb. 7, 1995. Such materials typically have a low tensile strength and/or low structural integrity. It is difficult to bond to such materials using adhesives because the structural integrity is often not as strong as the adhesive bond. As a result, only the portions of these materials that are in direct contact with the adhesive will remain bonded to other materials. The remainder of the material will readily separate from the material to which it is bonded. Such materials cannot be bonded using heat bonds because such foams are thermoset polymers. Once they are formed, they cannot be remelted. Instead, when heat is applied to such foam materials, they will char rather than melt and flow, which is needed for heat bonding. Such foam material likewise cannot be pressure bonded since the thermoset foam material has no ability to flow and be fused under pressure.

U.S. Pat. No. 4,473,611 entitled "Porous Polymeric Material Containing a Reinforcing and Heat-Sealable Material" issued to Haq on Sep. 25, 1984 describes one prior effort to bond materials to a highly porous polymeric material prepared by polymerization of a high-internal phase emulsion. The Haq reference discloses providing such a material with the ability to form heat seals by incorporating thermoplastic fibrous, particulate, or foraminous material therein. An article such as a wipe is formed by sandwiching the modified porous polymeric material between two heat sealable substrates, and heat sealing the first and second substrates to the heat-sealable reinforcing material in the intermediate highly porous polymeric material. The method of making the porous polymeric material described in the Haq patent, however, requires the addition of thermoplastic material. This complicates the process of making the porous polymeric material.

Other types of materials used in the manufacture of absorbent articles frequently comprise thermoplastic materials. U.S. Pat. No. 4,854,984 entitled "Dynamic Mechanical Bonding Method and Apparatus" issued to Ball, et al. on Aug. 8, 1989 discloses a method and apparatus for dynamically mechanically bonding together a plurality of laminae by feeding the laminae through a pressure biased nip between a pair of rolls, at least one of which has a relief pattern thereon. The method described in the Ball, et al. patent has been used with great commercial success. Still, the search for improved methods of bonding materials has continued.

Thus, a need exists for improved methods of bonding materials, especially those used in absorbent articles. For example, a need exists for an improved method of bonding materials for use in absorbent articles that cannot be bonded by known bonding techniques, and in particular for a method that does not require the addition of thermoplastic materials to the material in issue in order to bond other materials thereto. A need also exists for a method of bonding through relatively thick materials during the manufacture of absorbent articles. In addition, a need also exists for methods of bonding which are able to create a virtually unlimited number of bonding patterns in the materials to be bonded.

SUMMARY OF THE INVENTION

In one aspect, the present invention is directed to a method of bonding a laminate. The method includes the following steps:

(a) providing an anvil roll and a pattern roll, the rolls being capable of counter-rotating in relation to each other, the anvil roll having an anvil roll outer surface and the pattern roll having a pattern roll outer surface, at least one load bearer member disposed between the pattern roll outer surface and the anvil roll outer surface, the load bearer member having a bearer height, at least one pattern element extending from the outer surface of the pattern roll, the pattern element having a pattern height, the bearer height being greater than the pattern height, effecting a no-load gap between the pattern element and the outer surface of the anvil roll;

(b) providing a loading force to press the rolls to each other to effect a static load gap between the pattern element and the outer surface of the anvil roll, the static load gap being smaller than the no-load gap;

(c) providing the laminate between the outer surface of the pattern roll and the outer surface of the anvil roll; and (d) rotating the bonding rolls at a tangential velocity to compress the laminate between the pattern element and the outer surface of the anvil roll to effect a bond in the laminate.

In another aspect, the present invention is directed to an apparatus for bonding or embossing of a laminate. The apparatus includes an anvil roll and a pattern roll. The rolls are capable of counter-rotating in relation to each other. The anvil roll has an anvil roll outer surface and the pattern roll has a pattern roll outer surface. The apparatus further includes at least one load bearer member disposed between the pattern roll outer surface and the anvil roll outer surface. The load bearer member has a bearer height. The apparatus further includes at least one pattern element extending from the outer surface of the pattern roll. The pattern element has a pattern height. The bearer height is greater than the pattern height.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

FIG. 12A is schematic front elevation view of a first preferred embodiment of the methods and apparatus of the present invention showing an anvil roll and a pattern roll having continuous load bearing members, wherein the height of the continuous load bearing members is greater than the height of the pattern elements.

FIG. 12B is a schematic side elevation view of the apparatus of FIG. 12A.

DETAILED DESCRIPTION OF THE INVENTION

Figure 1:
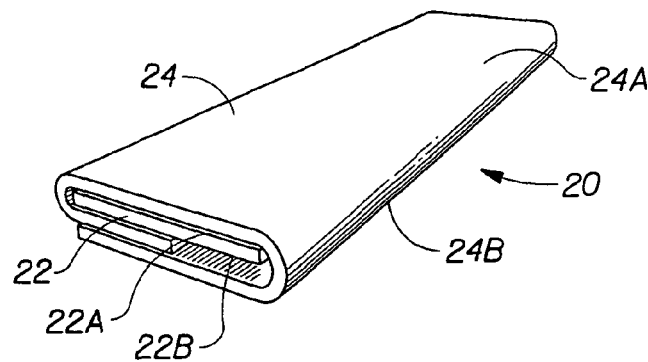
FIG. 1 is a perspective view of a composite web of material comprising an incompatible absorbent foam material that will be bonded and shaped into an absorbent tube for a sanitary napkin using the methods of the present invention.

The present invention relates to the methods of bonding materials for use in absorbent articles, although the techniques described herein may be used to bond materials used in other types of articles. In preferred embodiments, the present invention relates to such methods which are used in the manufacture of absorbent articles such as sanitary napkins, pantiliners, tampons, absorbent interlabial devices, diapers, incontinence devices, wipes, and the like.

There are numerous aspects of the present invention. In one aspect, the present invention relates to a method of bonding through incompatible materials during the process of making a composite structure comprising several materials. As used herein, the term "incompatible materials" refers to materials to which it is difficult to bond other materials to using conventional bonding techniques. In another aspect, the present invention relates to improvements that allow the method to be used to bond through relatively thick materials (e.g., materials having a thickness of greater than or equal to about 2, 3, or 4 mm). In another aspect, the present invention relates to methods of bonding which are able to create a virtually unlimited number of bonding patterns in the materials to be bonded. In still another aspect, the present invention relates to methods of bonding that utilize a compression step to improve bond formation. In still another aspect, the present invention relates to methods of bonding that utilize a step of slitting a material through which the bonds are made.

It should be understood that the embodiments described in the specification are expressed in terms of preferred embodiments so that the length of this specification is not excessive. It should be understood that the present invention is not intended to be limited to such embodiments. It should also be understood that the aspects of the methods described herein can be combined in a single process, or they can be used individually, or in any desired combination. It should further be understood that the inventors consider all such uses or combinations of these aspects to potentially comprise separate patentable inventions, and that the scope of such inventions is intended to be as broad as the prior art permits. The scope of such inventions is intended to be limited by the claims only, and not by the preferred embodiments described herein.

In particularly preferred embodiments, the methods of bonding materials described herein may also be used to provide the absorbent articles (or other types of articles), or portions thereof, with unique three dimensional shapes by using the bonding process to apply external forces to portions of the articles to shape the same.

1. Description of One Non-Limiting Embodiment of the Method of The Present Invention For Use in Making A Tube of Absorbent Material for a Compound Sanitary Napkin.

The method of the present invention can be used to bond many different materials for use in many different types of articles, including absorbent articles. FIGS. 1–8 show one particularly preferred use of the method of the present invention. FIGS. 1–8 show a process for making a tube of absorbent material for placement on the body-facing side of a base pad to form a compound sanitary napkin. A compound sanitary napkin comprises a primary menstrual pad (the tube of absorbent material) which is joined to a panty protector (the base pad). The tube of absorbent material is bonded and shaped by the method of the present invention. The final product is shown in FIG. 13.

The drawings show a number of steps that take place before (and after) the step of bonding the materials comprising the tube of absorbent material. It should be understood that a number of these steps are optional, and are shown since they are useful in making the absorbent product shown in FIG. 13. All uses of the method of the present invention need not include these optional steps. It should be understood that the method of the present invention is not limited to the method shown in FIGS. 1–8, and that the method shown in FIGS. 1–8 is merely exemplary.

A. Assembling the Components.

Figure 13:
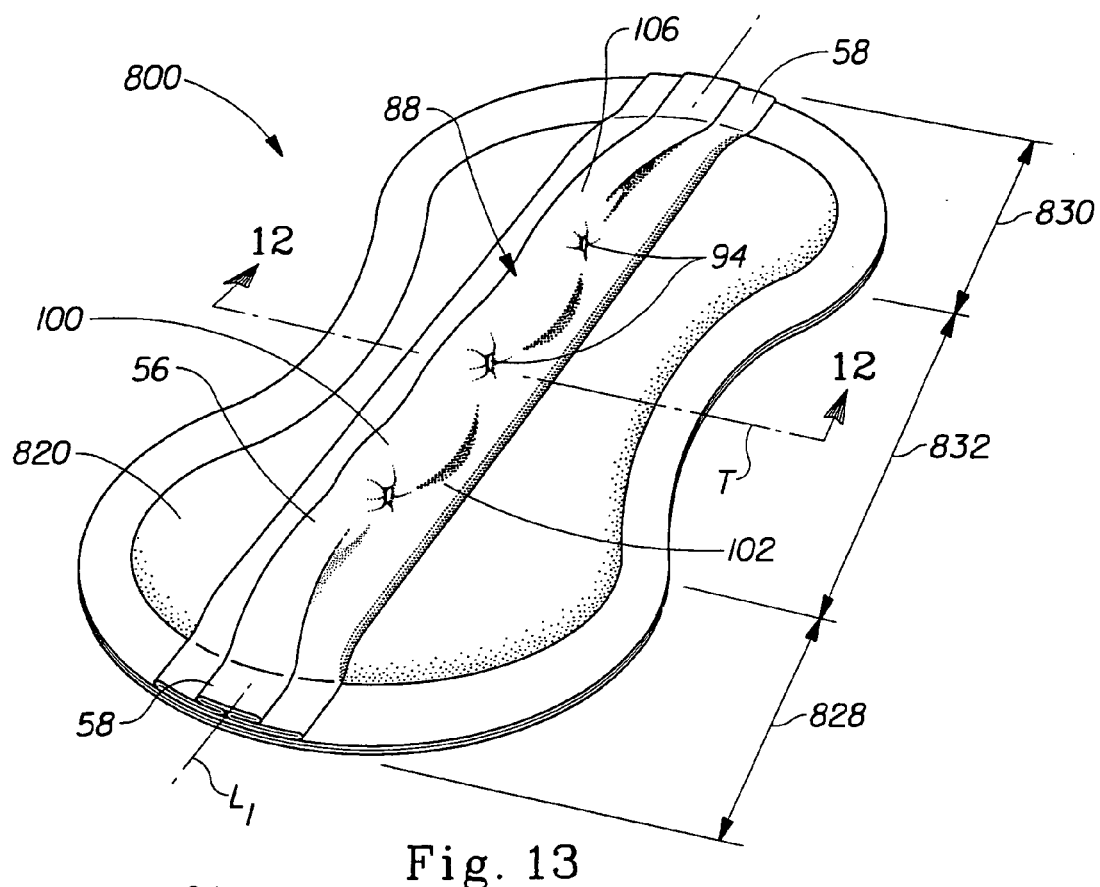
FIG. 13 is a perspective view of a compound sanitary napkin having a tube of absorbent material on the body-facing side thereof, which was bonded and shaped by the methods of the present invention.

FIG. 1 shows a composite web of material 20 that will be bonded using the methods of the present invention, and shaped into the absorbent tube for use in the sanitary napkin shown in FIG. 13. The composite web of material 20 shown in FIG. 1 comprises a first material, such as first web of material 22 that is incompatible with bonding using conventional techniques, such as adhesives, heat and/or pressure, and ultrasonics. The first web of material 22 may, thus, also be referred to as the "bonding incompatible material" or "web of incompatible material". The web of incompatible material 22 has a first surface 22A and a second surface 22B.

The incompatible first material 22 can be any suitable material. Preferably, the web of incompatible material 22 is an absorbent material, although substantially non-absorbent incompatible materials can be bonded using the methods of the present invention. The web of incompatible material 22 may, but need not be, compressible and/or resilient. Preferably, in this aspect of the invention, the first material 22 comprises a compressible and resilient, porous absorbent material. The first material 22 is also not limited to materials in the form of webs. The first material 22 can be in any suitable form. For instance, the first material 22 can be in the form of a mass of particles or fibers, a laminate, one or more layers, strips, sheets, blocks, or webs. Preferably, to make the tube of absorbent material shown in the drawings, it is in the form of a web.

The web of incompatible material 22 has a first bondability (ease, or degree to which it is capable of bonding to other materials or having other materials bond to it). The web of incompatible material 22 may, but need not be, completely incompatible with conventional bonding techniques. For example, it may be a material to which other materials are merely not readily bondable using such techniques. The bondability of a material can be determined by measuring the force required to separate the material from a bond, or attempted bond with another material. For the purpose of this definition, the separation occurs under the forces at which the two materials can be peeled apart, or the force at which the incompatible material's structural integrity breaks down during the process of attempting to separate the materials, whichever occurs first.

The web of incompatible material 22 may be a material that other materials are not readily bondable to for one or more reasons. Most often, such materials are incompatible with conventional bonding techniques because of their structural integrity or composition. One type of incompatible material is a porous polymeric absorbent foam material made from a high internal phase emulsion (or "HIPE" foam). Absorbent foam materials that have these characteristics are described in the patent literature, and include, but are not limited to the following patents: U.S. Pat. No. 5,260,345 issued to DesMarais, et al. on Nov. 9, 1993; U.S. Pat. No. 5,268,224 issued to DesMarais, et al. on Dec. 7, 1993; and U.S. Pat. No. 5,387,207 issued to Dyer, et al. on Feb. 7, 1995. Such materials may have a low tensile strength and/or low structural integrity and/or low level of elongation before breaking.

It is difficult to bond other materials to these absorbent foam materials using adhesives because the structural integrity of such materials is often not as strong as the adhesive bond. As a result, only the portions of the incompatible material that are in direct contact with the adhesive will remain bonded to other materials. The remainder of the incompatible material will readily separate from the material to which it is bonded. In addition, the foam materials described in the patents listed above cannot be bonded to other materials using heat bonds because these foams are thermoset polymers. Once they are formed, they cannot be remelted. Instead, when heat is applied to these foam materials, they will char rather than melt and flow, which is needed for heat bonding. These foam materials cannot be pressure bonded to other materials since the thermoset foam material does not have the ability to flow and be fused under pressure.

The web of incompatible material 22 may, thus, also be referred to as a material that is not readily bondable. In some instances, it may also be referred to as being non-heat sealable, free of thermoplastic material, and/or as a material having a low structural integrity. It should also be understood that the use of an incompatible material is only important in the aspect of the present invention that deals with a method of bonding incompatible materials. In other aspects of the method described herein, it is not necessary to use an incompatible material. In such other aspects, any suitable material, including a wide variety of absorbent materials, can be used.

In the embodiment shown in the drawings, the web of incompatible material 22 is a web of absorbent foam material such as one of those foam materials described in the foregoing patents. The web of incompatible material 22 in the embodiment shown in FIG. 1 is at least partially wrapped in a second web of material 24. The second web of material 24 has a second bondability that is higher than the bondability of the web of incompatible material 22. That is, it can be more readily bonded to other materials (or to itself) using conventional bonding techniques. The second web of material 24 may also be referred to herein as a "carrier web" or a "bondable web". In the embodiment shown in FIG. 1, the second web of material 24 is preferably completely wrapped around the web of incompatible material 22 so that the second web of material 24 has an "e"-folded configuration in cross-section.

The second web of material 24 can be any material that is capable of being bonded to itself, or to at least some other materials used in the types of absorbent articles described herein by heat or pressure, adhesives, or ultrasonics. The second web of material 24 may be manufactured from a wide range of materials such as woven and nonwoven materials; polymeric materials such as apertured formed thermoplastic films, apertured or unapertured plastic films, and hydroformed thermoplastic films; porous foams, reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers); bicomponent fibers (that is, fibers having a core of one material which enclosed in a sheath made of another material), or from a combination of natural and synthetic fibers. Preferably, in the embodiment shown, the second web of material 24 at least partially comprises thermoplastic material. In other embodiments, however, particularly if adhesives or other types of bonding are used, the second material 24 need not comprise thermoplastic material. For instance, second material 24 can be a cellulosic material that can be bonded to itself by hydrogen bonding.

In still other embodiments, the second web of material 24 can be replaced by a material that is in a form other than a web of material. For example, the second web of material 24 may be replaced by a bondable layer or coating such as an extruded glue coating or a polymeric coating that is applied to the web of incompatible material 22. Glues, particularly hot melt adhesives, are similar to thermoplastic materials in that they are capable of being bonded using this aspect of the method of the present invention. Certain silicones, particularly if they have low enough melting points, will also be capable of being bonded as described herein. For this reason, the second web of material 24 may be referred to as the "second material" so that it is clear that materials other than webs are included.

In the preferred embodiment shown in the drawings, the second material 24 preferably comprises a material that is also suitable for use as a wrapping for the absorbent material in an absorbent article. For example, the second material 24 can serve as a containment web for containing absorbent material in the absorbent article, as a cover or topsheet for the absorbent article, or as a backsheet for the absorbent article. For the embodiment shown in FIGS. 1–8 and 13, the second material 24 comprises a containment web made of spunbonded nonwoven material. One particularly preferred spunbonded nonwoven material is a 19 g/yd$^2$ (22.5 g/m$^2$) spunbonded polypropylene nonwoven material referred to as product No. 065MLPV60U (or "P-9") obtained from Fiberweb, North America of Washougal, Wash. Another particularly preferred nonwoven material is a spunbonded polyethylene nonwoven material known as COROLIND sold by Corovin GmbH, Peine, Germany, which can be obtained in two basis weights, 23 gsm and 30 gsm.

Although the second web of material 24 is wrapped around the web of incompatible material 22 in an e-folded configuration, it should be understood that if a web of material is used, the second web of material 24 is not limited to wrapping the web of incompatible material 22 in an "e"-folded configuration. The relationship between the web of incompatible material 22 and the second web of material 24 is preferably one in which a web of material having a higher bondability than the web of incompatible material 22 is merely at least adjacent to two opposing surfaces (e.g., 22A and 22B shown in FIG. 1) of the web of incompatible material 22. Thus, in other embodiments, the second web of material 24 may only be partially folded or wrapped around the web of incompatible material 22. The second web of material 24 can be folded or wrapped around the incompatible material 22 in any other suitable configurations. Other suitable configurations include, but are not limited to C-folded configurations, and the like.

It is also not necessary that the second web of material 24 be limited to a single web that wraps the web of incompatible material 22. One (or more) webs of material may be placed adjacent to each surface 22A and 22B of the web of incompatible material 22. For example, in other embodiments, there may be two separate webs of second material 24, one of which is placed adjacent to each surface 22A and 22B of the web of incompatible material 22. The two webs of second material 24 may be the same type of material and have the same characteristics. In other embodiments, the two webs of material that are placed adjacent to each surface 22A and 22B of the web of incompatible material 22 may differ. For example, they may be different types of materials, or they may be the same basic types of materials, but have different characteristics (such as caliper, etc.).

In still other embodiments, the second material 24 need not be a web that is as wide or as long as the web of incompatible material 22. For instance, the second material 24 can be in the form of strips, stripes, patches, or pieces located at the desired location for the bond points. Thus, the second material 24 need only cover a portion of the first and second surfaces 22A and 22B of the web of incompatible material 22.

B. Optional Intermediate Steps (1) Forming the Incompatible Material Into Particulate Material.

In the preferred embodiment of the process of making the tube of absorbent material shown in FIGS. 1–8, before the bonding and shaping take place, the web of incompatible material 22 will be formed into particulate material while it is inside the second web of material 24. This will be done by the process described in the commonly-assigned U.S. patent application Ser. No. 09/027,379 entitled "Method of Making Slitted or Particulate Absorbent Materials" filed in the name of Ronald R. McFall, et al. on Feb. 20, 1998.

In such a case, it is preferable that the second web of material 24, not only be more bondable than the web of incompatible material 22, but also that it have a higher yield to break point than the web of incompatible material 22. This operation (forming the incompatible material into particulate material) is an optional step that is preferably performed prior to carrying out the step of bonding, which is highly preferred for making the tube of absorbent material for the sanitary napkin shown in FIG. 13. It should also be understood that the step of forming the incompatible material into particulate material is not limited to being carried out before the bonding step. The step of forming the incompatible material into particulate material can alternatively be carried out at the same time as, or after, the bonding step, if desired. The reasons for this optional step being preferred are discussed in greater detail below.

Figure 2:
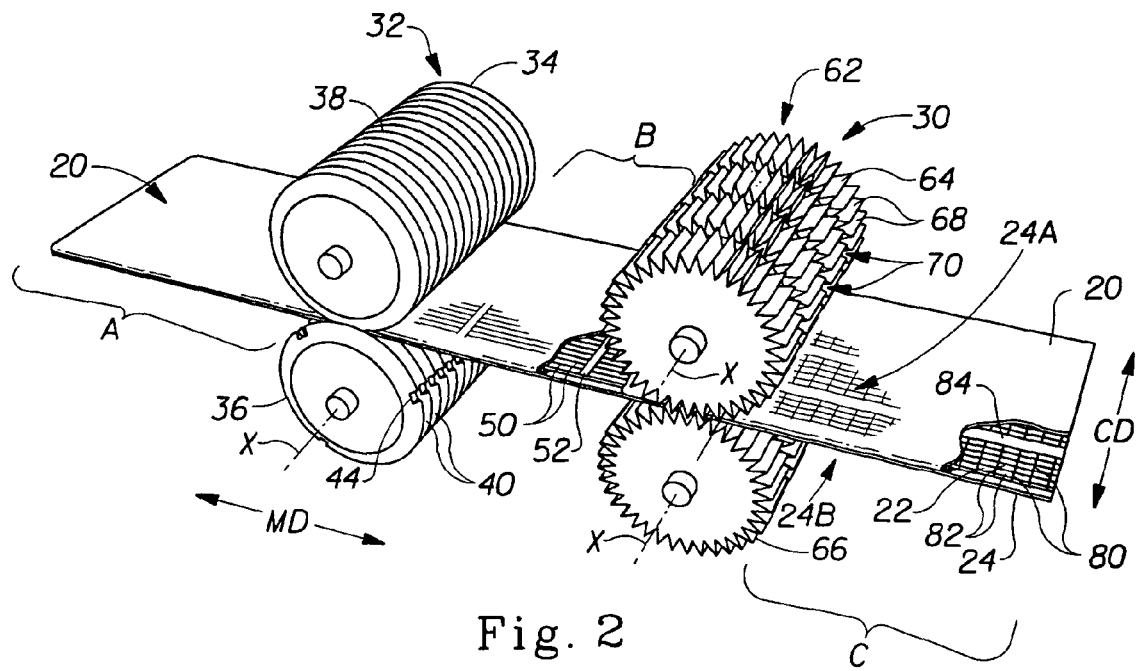
FIG. 2 is a perspective view of an apparatus used to form the absorbent material in the composite web shown in FIG. 1 into particulate material in an optional, but preferred step of making the absorbent tube.

The optional process of forming the incompatible material 22 into particulate material comprises several steps. Although there are several embodiments of this optional process (and the apparatus used therein), a preferred embodiment of the process and apparatus are shown in FIG. 2. The process and apparatus shown in FIG. 2 are used to form the incompatible material 22 into particulate material by mechanically straining the incompatible material 22.

A first step involves providing a "carrier web" having a first yield to break point under tensile forces is provided. (In the embodiment described herein, the second web of material 24 serves as the carrier web.) The web of material for forming into particulate material (which in this case is the web of incompatible material, foam absorbent material 22) and the carrier web are then formed into a composite structure, such as composite web 20. The foam absorbent material 22 has a second yield to break point under tensile forces that is lower than the yield to break point of the nonwoven carrier web 24. Thus, the first two steps of forming the incompatible material 22 into particulate material have already been performed in preparation for the methods of bonding described herein.

An apparatus for mechanically straining the composite web 20 is provided. The apparatus preferably comprises a device that has at least one component with a patterned surface thereon. The composite web 20 is then preferably subjected to a mechanical straining process using the apparatus by impressing the patterned surface thereon into the composite web 20 so that the foam absorbent material 22 is at least partially formed into particulate material without forming the carrier web (the second web of material) 24 into particulate material.

The apparatus 30 for mechanically straining the composite web 20 shown in FIG. 2 comprises two pairs of cylindrical rolls, a first pair of rolls 32 and a second pair of rolls 62. Each of the rolls has a patterned surface thereon. The patterns are preferably formed by a plurality of ridges and valleys on the rolls that define a plurality of triangularly shaped teeth. Suitable patterned rolls for use as the first and second pair of rolls 32 and 62 of the apparatus shown in FIG. 2 (though not for this purpose of forming incompatible material into particulate material) are described in greater detail in U.S. Pat. No. 5,518,801 entitled "Web Materials Exhibiting Elastic-Like Behavior" issued to Chappell, et al. on May 21, 1996.

In the preferred embodiment shown, the rolls in the first pair of rolls 32 preferably have triangularly-shaped teeth that are formed by ridges and valleys that are oriented around the circumference of the rolls. The teeth preferably have cross-sections in the form of isosceles triangles. The apex of the teeth may be slightly rounded, if desired. The top roll 34 and the bottom roll 36 in the first pair of rolls 32 are aligned so that the ridges 38 of the top roll 34 align with the valleys 40 on the bottom roll 36. The triangular-shaped teeth that form the ridges on the top roll 34 and the valleys on the bottom roll are spaced so that these teeth do not touch each other or fully "engage".

The teeth can be of any suitable size and pitch. The term "pitch", as used herein, refers to the distance between the apexes of adjacent teeth. In the preferred embodiment shown in the drawings, the depth (or height) of the teeth is preferably between about 0.1 inches and about 0.17 inches (about 2.5 mm to about 4.3 mm). The pitch is preferably between about 1 mm and about 5 mm, and more preferably is between about 1.5 mm and about 2.5 mm. The pitch of the teeth establishes the width of pieces into which the absorbent material is cut or chopped.

The bottom roll 36 may also comprises several evenly-spaced thin planar channels 44 on the surface of the bottom roll 36 that are oriented parallel to the axis, X, of the bottom roll. In this embodiment, the spaced apart channels 44 in the bottom roll 36 preferably have a width of 2 mm. The "length" of the teeth in the bottom roll 36 measured around the circumference of the bottom roll between the spaced apart channels is 8 mm. The rolls 34 and 36 are preferably driven in opposite directions.

The triangularly-shaped teeth on the top roll 34 and the valleys 40 on the bottom roll 36 should preferably be spaced so that they are partially intermeshing. The degree to which the teeth on the opposing rolls intermesh is referred to herein as the "engagement" of the teeth. The engagement of the teeth is the distance between a position where the apexes of the teeth on the respective rolls are in the same plane (0% engagement) to a position designated by plane where the apexes of the teeth of one roll extend inward beyond the plane toward the valleys on the opposing roll. The engagement of the teeth can be expressed as a percentage of the pitch (distance between the apexes of the teeth on one of the rolls), or in terms of a measured distance. Since the height of the teeth may be greater than the pitch, the engagement may be a value that is greater than 100% (for instance, if the engagement is greater than the pitch length). Preferably, the engagement is between about 15% and about 120% of the pitch length. The engagement expressed in terms of a measured distance is preferably between about 0.01 inch to about 0.07 inch (about 0.25 mm to about 1.8 mm), and more preferably is between about 0.04 inch to about 0.06 inch (about 1 mm to about 1.5 mm).

As shown in FIG. 2, at the stage designated A, the composite web 20 is fed in a machine direction (MD) into the nip between the rolls 34 and 36. The second web of material 24 at this stage of the process is serving as a carrier web. As a carrier web it holds and contains the web of incompatible material 22 which is about to be slit and formed into particulate material. The second web of material 24 wraps the outside of the web of incompatible material 22 so that the second web of material 24 faces the patterned surfaces on the rolls 34 and 36.

The rolls 34 and 36 subject the composite web 20 to a mechanical straining process by impressing the patterned surfaces thereon into the composite web 20. The mechanical straining process applies a force that is greater than the yield to break point of the web of incompatible foam absorbent material 22, but less than the yield to break point of the nonwoven carrier web (the second web of material (having the higher bondability)) 24 so that the web of incompatible foam absorbent material 22 is at least partially slit without slitting the carrier web 24.

FIG. 2 shows the condition of the composite web at stage B, after it passes through the nip between the first pair of rolls 32. As shown in FIG. 2, the carrier web 24 will have a pattern of corrugations formed therein that corresponds to the combination of the patterns on the adjacent rolls, 34 and 36. The carrier web 24, however, is not slit or cut. The intermediate web of foam absorbent material 22 has a plurality of slits 50 formed therein. The slits 50 are oriented in the machine direction (or "MD"). In the particular embodiment shown, the slits 50 are intermittent and separated by cross-machine direction (or "CD") bands of unslit material 52. This is due to the presence of the channels 44 on the bottom roll 36. The web of foam absorbent material 22 is slit while the carrier web 24 is not slit because the web of foam absorbent material 22 has a lower yield to break point than the carrier web 24, and breaks, under tensile forces (the straining process) while the carrier web 24 does not.

At this point in the process, (at stage B, between the first and second sets of rolls, 32 and 62) it is possible to perform additional operations on the composite web 20. For example, the composite web 20 can be cut into discrete lengths between the first and second sets of rolls 32 and 62. In other embodiments, the composite web 20 can be cut into discrete lengths by a cutting blade located on one of the rolls in the first set of rolls 32. The composite web 20 would be cut into lengths that correspond to the length of the tube desired for the sanitary napkin shown in FIG. 13.

Figure 3:
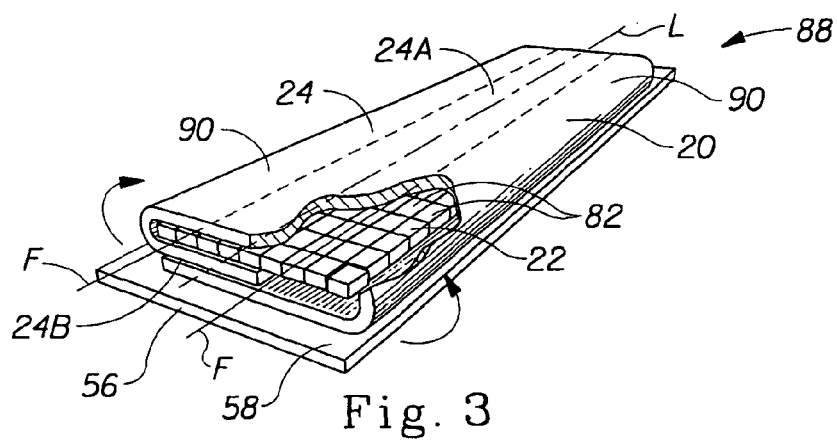
FIG. 3 is a partially fragmented perspective view of the composite web shown in FIG. 1 after it has been fed through the apparatus shown in FIG. 2 and the incompatible absorbent foam material has been formed into particulate material.

Further, an additional web (or webs) of material, such as a continuous web of apertured film topsheet material 56, can be joined to the composite web 20 between the first and second sets of rolls, 32 and 62. Alternatively, such an additional material could be cut into individual pieces and joined to the composite web 20 between the first and second set of rolls. The joinder of the apertured film topsheet material 56 to the composite web 20 is shown in FIG. 3. It has also been omitted from FIG. 2 for simplicity of illustration. The apertured film topsheet material 56 is preferably joined to the composite web 20 by adhesives. This forms a structure that will be referred to herein as the "tube forming composite" (or "tube forming composite web") 88.

The second set of rolls 62 of the apparatus 30 for mechanically straining the composite web comprises top and bottom rolls, 64 and 66, respectively. Each of these rolls also has a pattern on its surface. As shown in FIG. 2, the top roll 64 has ridges that run parallel to the axis, X, of the top roll 64. The ridges define a plurality of triangular-shaped teeth 68. The top roll 64 may also have several spaced apart channels 70 that are oriented around the circumference of the cylindrical roll.

FIG. 2 shows that when the composite web 20 leaves the nip between the second set of rolls 62, at least a portion of the foam absorbent material 22 is further provided with a plurality of slits 80 that are oriented in the cross-machine direction. This initial slitting in the machine direction and subsequent slitting in the cross machine direction results in the absorbent material 22 being formed or chopped into a plurality of particles 82. The foam absorbent material 22 can optionally have unslit strips 84 left therein due to the presence of the channels 70 in the second pair of rolls 62, in addition to any cross-machine direction bands of unslit material due to the presence of the channels 44 on the bottom roll 36 in the first pair of rolls 32.

Again, the nonwoven carrier web 24 is not slit, but has another pattern formed therein. The overall pattern formed therein resembles a grid with a combination of the impressions created by the first and second sets of rolls 32 and 62. The apertured film topsheet 56 will have a pattern formed therein that resembles that of the second pair of rolls 62.

FIG. 3 shows the composite web 20 after it has been fed through the apparatus shown in FIG. 2. As discussed above, a sheet of apertured film topsheet material 56 has preferably been joined to the individual lengths of the composite web 20 between the first and second pairs of rolls. FIG. 3 shows that the sheet of apertured film topsheet material 56 is preferably of a size that is about the same width as, but longer than, the individual lengths that the composite web 20 was cut into. The apertured film 56 extends beyond the ends of the individual lengths of composite web material so that the tube of absorbent material, once formed, can be more easily attached to the sanitary napkin, by attaching only the ends of the same to the sanitary napkin.

It should be understood that in FIG. 3, the pattern impressed into the nonwoven material 24 by the first and second sets of rolls has been omitted or simplicity. In addition, the incompatible foam absorbent material 22 is shown as comprising only particles 82 for simplicity (that is, no unslit strips are shown as being left in the incompatible material 22). Such an embodiment could be created by providing the rolls on the first and second sets of rolls 62 with continuous teeth and omitting the valleys 40 and channels 70 between the teeth.

(2) Optional Step of Folding the Tube Forming Composite Web.

The next step in making the tube of absorbent material for the sanitary napkin shown in FIG. 13, is folding the combination of the composite web 20 and the sheet of apertured film topsheet material 56, the tube forming composite web 88. These optional but preferable folding steps are shown in the next few drawing figures.

Figure 4:
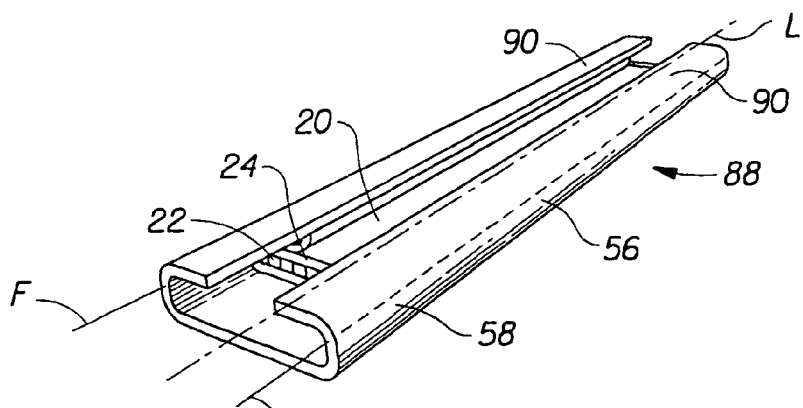
FIG. 4 is a perspective view of the composite web shown in FIG. 3 after the side margins have been folded in a first optional folding operation.

FIG. 3 shows the longitudinally-oriented folding lines, F, about which the longitudinal side margins 90 of the tube forming composite web 88 will initially be folded. FIG. 4 shows the tube forming composite web 88 after the side margins 90 thereof have been folded along folding lines F in a first folding operation to form a "C"-folded structure.

Figure 5:
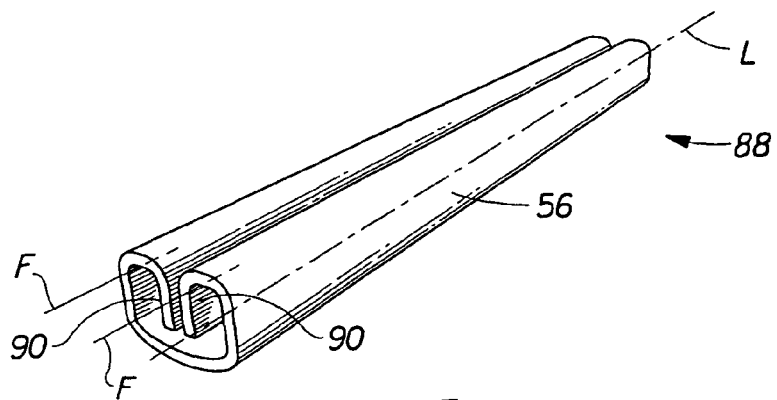
FIG. 5 is a schematic perspective view of the composite web shown in FIG. 3 after it has been folded in a second optional folding operation.
Figure 6:
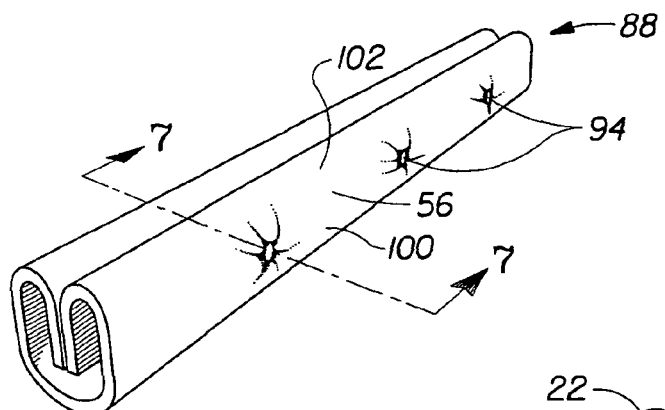
FIG. 6 is a schematic perspective view of the composite web shown in FIG. 5 after portions thereof have been bonded together.

FIG. 5 shows the tube forming composite web 88 after it has been folded in a second folding operation. As shown in FIG. 5, the tube forming composite web 88 has been folded along its longitudinal centerline, L. As a result, the previously-folded longitudinal side margins 90 are brought adjacent to each other, and the longitudinal side margins 90 of the tube forming composite web 88 are tucked inside the folded tube forming composite web 88. As shown in FIG. 5, the folded longitudinal side margins 90 lie adjacent to the longitudinal centerline, L, of the tube forming composite web 88. The folded tube forming composite web 88 shown in FIG. 5 is now ready to be bonded using the methods of the present invention. (The steps shown in FIGS. 2–5 were all optional, but preferred steps for making a tube of absorbent material for the sanitary napkin shown in FIG. 13.)

C. Bonding (and Shaping) the Incompatible Material.

(1) In General.

Figure 7:
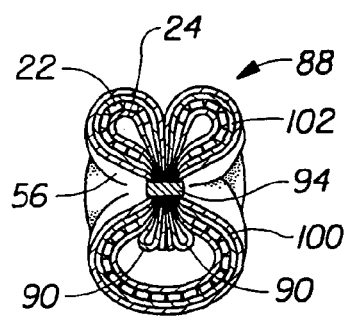
FIG. 7 is a simplified cross-sectional view of the web shown in FIG. 6 taken through one of the bond sites along line 7—7 of FIG. 6.

In order to bond (and shape) the incompatible absorbent foam material 22, in the most general sense, the web of material having the higher second bondability (the nonwoven) 24 is positioned to the outside of the incompatible material (the absorbent foam material) 22. The cross-section of the actual structure being bonded (as shown in FIG. 7) is somewhat more complicated than that, but for the purposes of the present description, the above-described general relationship (with the web of material having the higher second bondability positioned outside of the web of incompatible material) is preferably present.

The incompatible material, absorbent foam material 22, with the web of material having the second higher bondability, the nonwoven web 24, on the outside of the same, is preferably bonded with a plurality of autogenous bonds 94. The term "autogenous", as used herein, refers to bonding without adhesives or some other additional material (that is, additional to the components to be bonded) such as a stitched thread. The methods described herein, however, are not intended to be limited to methods which preclude adhesive augmentation of such autogenous bonding, or adhesive bonding per se.

The bonds 94 preferably penetrate the incompatible absorbent foam material 22. The bonds 94 preferably join one portion of the nonwoven web 24 to another portion of the nonwoven web 24 on the opposite side of the incompatible foam material 22. In the embodiment shown in the drawings, the bonding serves as a step in the methods of the present invention directed to bonding incompatible materials, and also serves to provide the tube of absorbent material with a unique three dimensional shape.

In carrying out the methods of the present invention, any suitable number of bonds 94 can be used. The bonds 94 can also be placed in any suitable location. For making the tube of absorbent material for the sanitary napkin in FIG. 13, two to five bonds 94 are preferably used. In the embodiment shown in the drawings, three bonds 94 are used. The bonds 94 are preferably spaced about 1.75 inches (about 4.4 cm) apart, and are located about 17 mm from the fold made along the longitudinal centerline, L, of the tube forming composite web 88.

The preferred autogenous bonding process can be accomplished using heat and/or pressure, or by ultrasonics. Suitable techniques for heat and/or pressure bonding, and dynamic bonding in particular, are described in greater detail below. Suitable techniques for ultrasonically bonding are described in Procter & Gamble U.S. Pat. No. 4,430,148 entitled "Ultrasonic Bonding Process" issued to Schaefer on Feb. 7, 1984 and U.S. Pat. No. 4,823,783 entitled "Adhesive-Free Bonding of Continuously Moving Webs to form Laminate Web and Products Cut Therefrom" issued to Willhite, Jr. et al. on Apr. 25, 1989. Suitable equipment for ultrasonic bonding is available from Branson Ultrasonics of Danbury, Conn. The ultrasonic bonding apparatus is preferably equipped with a plate which has pattern elements similar to those described below for the dynamic bonding process. It should be understood, however, that ultrasonic bonding may be less preferred (than the dynamic bonding process) for use in bonding some of the higher caliper structures described herein.

A dynamic bonding process has several other advantages over ultrasonic bonding processes. First, it can be a continuous process which is capable of operating at high speeds. By contrast, ultrasonics generally require the use of an apparatus having at least one static head which provides a fixed dwell time to form the bond. Thus, in ultrasonic bonding processes, the web to be bonded has to be stopped for a period to complete the bond. Second, ultrasonic bonding processes are not as suitable for bonding through materials having thicknesses over certain amounts (e.g., up to, or greater than or equal to, about 4 mm). The dynamic bonding process described herein, in the other hand, can easily bond through materials having such thicknesses.

The slitting or forming the absorbent material 22 into particulate material in the prior step is advantageous in the bonding process. This is because the methods used to form the slit or particulate material may provide a continuous clear path for the bonds to penetrate through the absorbent material. This is particularly the case if the bonds are aligned with the slits or the spaces between the particles. This is most likely to occur where the slit or particulate material is adhered to a carrier web. Prior methods of chopping absorbent material which merely chop the absorbent material and blow it by compressed air into a closed tube will result in a random distribution of the chopped particles. Such methods will not form the clear path for the bonding process described herein.

The dynamic bonding process, as discussed above, involves bonding portions of the second web of material (nonwoven covering) 24 on each side of the absorbent foam material 22 together. The apertured film topsheet material 56 can also have portions which are dynamically bonded together. The apertured film topsheet material 56 can be bonded in addition to, or alternatively to bonding portions of the nonwoven covering 24 together. In the dynamic bonding process, at least one of the materials to be bonded (the nonwoven covering 24 or the apertured film topsheet 56 material) preferably comprises thermoplastic material. (It should be understood that, for simplicity, the bonding will be expressed below in terms of bonding portions of the nonwoven covering 24 together, even though portions of the apertured film topsheet material may be similarly bonded in the process.)

Figure 8:
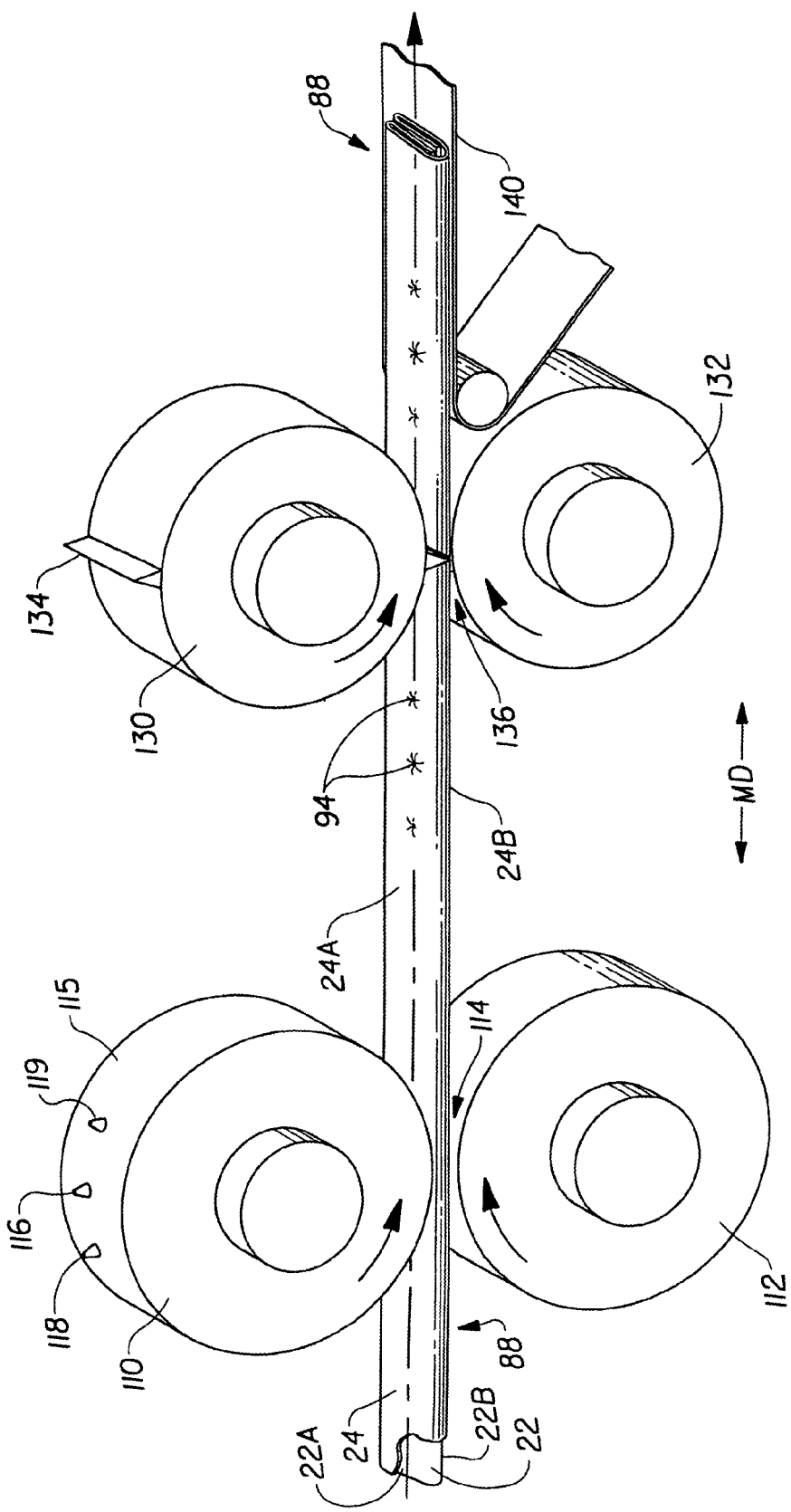
FIG. 8 is a schematic perspective view of one embodiment of a step of the method which is used to bond the tube of absorbent material for a sanitary napkin, with the patterned roll shown in a simplified manner.

FIG. 8 shows the process in which a first portion 24A of the cover material 24 is preferably bonded through the tube forming composite web 88 to a second portion 24B of the cover material. The apparatus used for bonding the tube forming composite web 88 preferably comprises a pair of cylindrical rolls 110 and 112. Preferably, at least one of the rolls, patterned roll 110, has a relief pattern on its surface. The patterned roll 110 is shown in a simplified manner in FIG. 8, and in greater detail in FIG. 12. (FIG. 12, however, shows a roll with a relief pattern thereon that is slightly different from the pattern shown in FIG. 8.)

Figure 12:
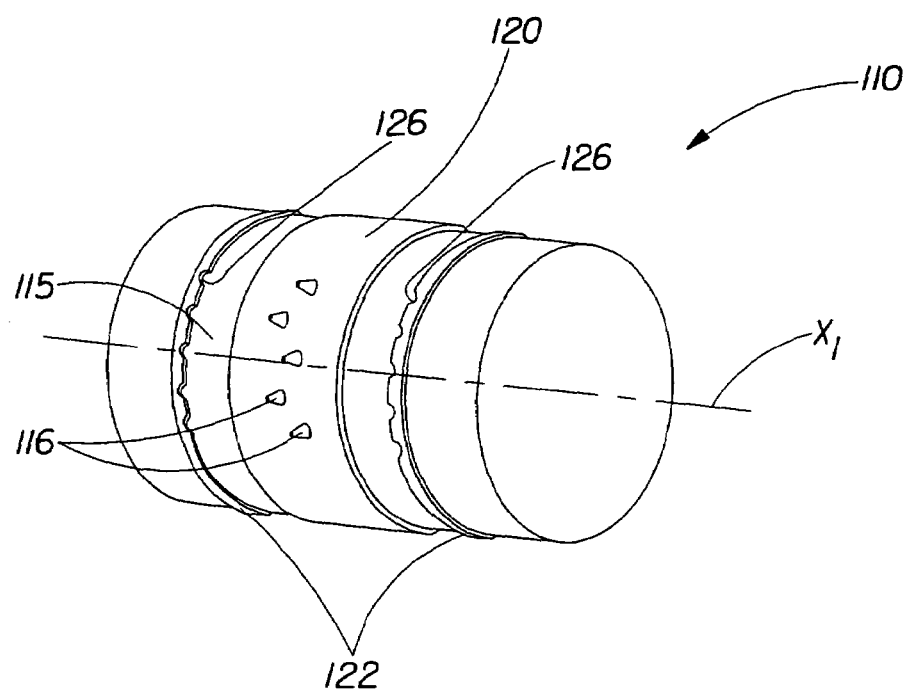
FIG. 12 is a perspective view showing the surface of a patterned roll used in one embodiment of the methods of the present invention with continuous load bearing members thereon.

As shown in FIG. 12, the patterned roll 110 has a cylindrical surface 115, and a plurality of protuberances or pattern elements (or "pattern element segments", "projections", or "nubs") 116 which extend outwardly from the surface 115. The relief pattern formed by the pattern elements 116 can be in any suitable configuration. It can be linear, curvilinear, or it can be comprised of linear segments and curvilinear segments. The relief pattern can be continuous or intermittent. The relief pattern can define an unlimited number of patterns and other types of designs. For example, it can define geometric shapes, arrows, words, etc. The land surfaces 118 on the pattern elements can also be provided in a wide variety of possible shapes. Suitable shapes for the land surfaces 118 include, but are not limited to, oval and circular.

In the embodiment of the apparatus shown, the relief pattern comprises a plurality of spaced apart pattern elements 116 having circular land surfaces 118. In the embodiment of the method shown in FIG. 8, the pattern elements 118 are arranged in an intermittent linear configuration.

While the present invention is intended to apply to bonds of any suitable shape and size, bond sizes that have been found to be suitable have a circular plan view configuration with a diameter of between about 0.25 mm to about 5 mm or more. In one embodiment, the bonds have a diameter of about 3 mm and an area of about 8 $mm^2$.

The pattern elements 116 have side walls 119 that are preferably not perpendicular with the surface of the cylindrical roll. Preferably, the side walls 119 of the pattern elements 116 form an angle of greater than 45° and less than 90°, preferably between about 70–90 degrees, with surface 115 of the cylindrical roll. Modifying the orientation of the side walls 119 of the pattern elements 116 is preferred due to the thickness of the materials being bonded, and the desire to avoid tearing the cover material 24.

The other roll 112, serves as an anvil member and, thus, may be referred to as anvil roll 112. The patterned roll 110 and the anvil roll 112 define a pressure biased nip 114 therebetween. Preferably, the anvil roll 112 is smooth surfaced. In other embodiments, however, both rolls 110 and 112 may have a relief pattern and/or pattern elements thereon. The patterned roll 110 and anvil roll 112 are preferably biased toward each other with a pre-determined pattern element loading of from about 20,000 psi (about 140 Mpa) to about 200,000 psi (about 1,400 MPa). In the embodiment shown in FIG. 8, the rolls are baised toward each other so that pressure in the nip 114 is preferably maintained at about 93,700 psi (about 656 Mpa). In this embodiment, the materials to be bonded are preferably being fed through the nip 114 at a relatively high rate of speed. The speed of the line is preferably about 383 feet/minute (about 117 m/minute).

The patterned roll 110 and the anvil roll 112 are preferably driven in the same direction at different speeds so that there is a surface velocity differential therebetween. The surface velocity differential preferably has a magnitude of from about 2 to about 40 percent of the roll having the lower surface velocity, more preferably between about 2 to about 20 percent. The anvil roll 112 is preferably operated at a surface velocity that is greater than the surface velocity of the patterned roll 110. It is also possible, however, at high line velocities, for the bonding to occur at zero velocity differential (that is, with the nip defining rolls having equal surface velocities).

The plural laminae comprising the tube forming composite web 88 is bonded by feeding it into the nip 114 between rolls 110 and 112. The preferred bonding process shown in the drawings penetrates through the tube forming composite web 88 and autogenously bonds the first portion 24A of the nonwoven cover material to the second portion 24B of the cover material 24. The bonds 94 are formed between the opposed portions of the nonwoven web of material 24 having the higher second bondability that are positioned outside the foam material 22.

Without wishing to be bound to any particular theory, the mechanism by which the bonding of the incompatible material is believed to occur is as follows. The pattern elements 116 of the bonding mechanism compress the incompatible absorbent foam material 22. This localized compression causes the incompatible absorbent foam material 22 to fracture and separate (move away from the pressure point) from the area of the pattern elements 116. The bonding mechanism slices through the incompatible material 22 or displaces the particles of incompatible material 22 so that there is a clear path for the bondable materials to bond together. Preferably, very little (if any) of the foam material 22 is actually left in the bond sites.

In addition to the penetration of the incompatible material by the bonds, the method described herein has several other important features. These features allow high caliper materials to be bonded, and enable the process to create a virtually unlimited number of bonding patterns in the materials to be bonded. The patterned roll 110 preferably has a compliant (or compressible) material 120 on its surface 115. The patterned roll 110 preferably also has a pair of load bearing members 122 on its surface 115. The purposes of these components are described below.

The purpose of the complaint material 120 is to compress the materials to be bonded so that the pattern elements 116 are less likely to puncture the cover material(s) 24. If the cover material(s) are punctured, the bonds will either not form, or a weak bond will form because the cover material will not be melted to form the bond. The compression step may occur prior to, or simultaneously with the bonding. The use of a compliant material is particularly preferred when the materials to be bonded are relatively thick. The complaint material can be omitted when the materials to be bonded are thinner. FIG. 12 shows that the compliant material 120 preferably surrounds the pattern elements 116.

Figure 9:
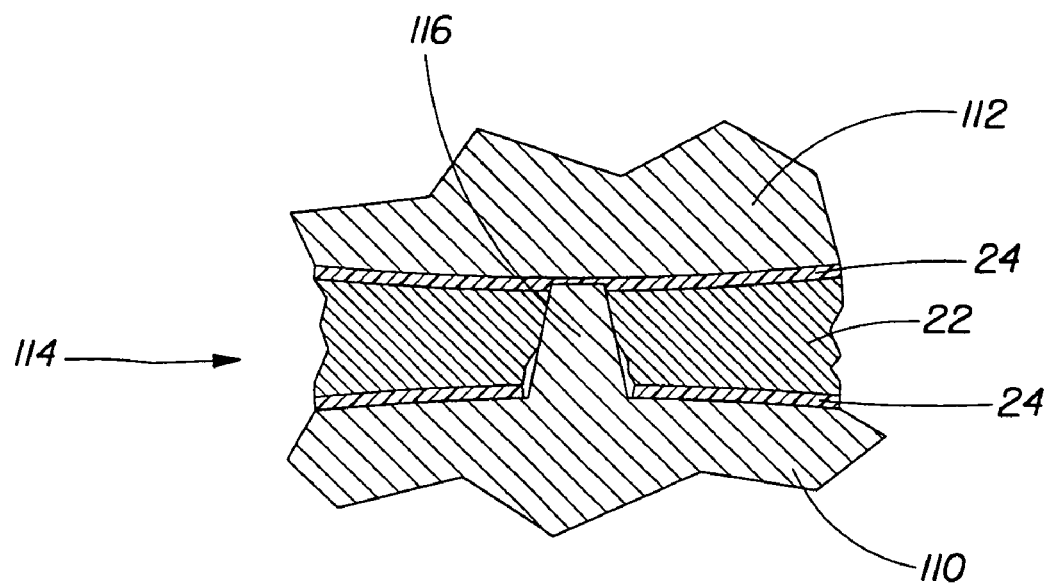
FIG. 9 is a simplified fragmentary schematic view showing a relatively high caliper material in the nip between a patterned roll and an anvil roll in which the patterned roll is not provided with a compressible material around its raised element.
Figure 10:
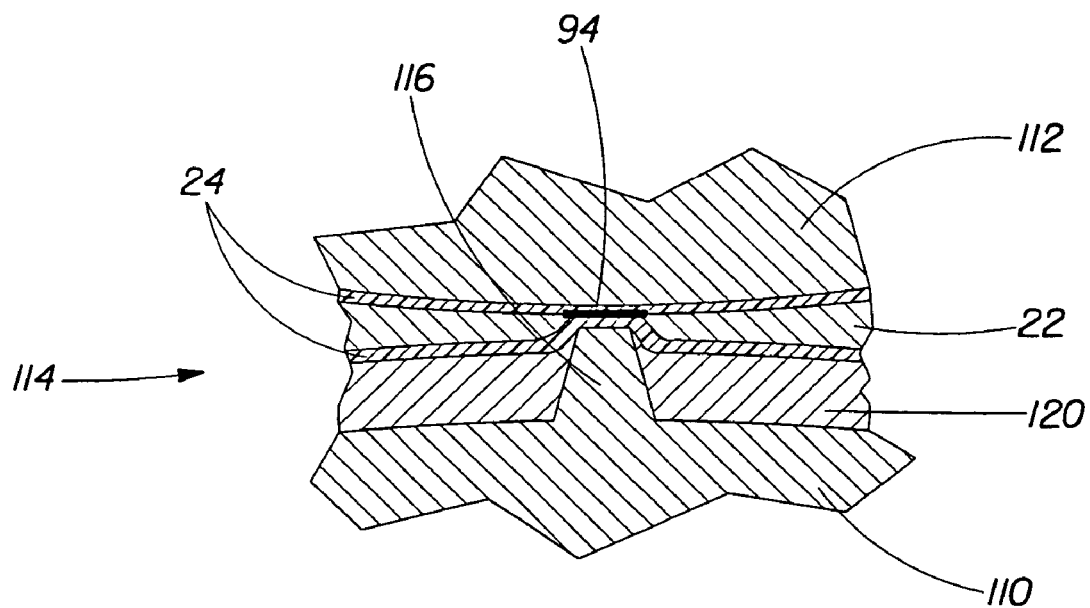
FIG. 10 is a simplified fragmentary schematic view showing a relatively high caliper material in the nip between a patterned roll and an anvil roll in which the patterned roll is provided with a compressible material around its raised element.

A comparison of FIGS. 9 and 10 shows the manner in which the complaint material 120 is believed to function. FIG. 9 shows a relatively thick material passing through the nip 114 between the patterned roll 110 and the anvil roll 112 without a compliant material surrounding the pattern element 116. As shown in FIG. 9, the pattern element 116 tends to puncture the materials to be bonded due to the high localized stresses in the materials to be bonded, particularly the cover material 24.

FIG. 10 shows the same relatively thick material passing through the nip 114 between the patterned roll 110 and the anvil roll 112 with a compliant material 120 surrounding the pattern element 116. As shown in FIG. 10, the compliant material 120 occupies space between the patterned roll 110 and the anvil roll 112. The compliant material 120 causes the materials to be bonded to be gradually compressed in the area of the pattern element 116. This brings both of the layers of the cover material 24 closer together during the bonding without applying added strain to the cover material 24. This allows the bond 94 to be made without tearing the cover material 24, or punching a hole through the foam material 22 situated between the layers of cover material 24.

The way this works can be visualized by thinking of the following analogy. The principle involved is similar to the problem of attempting to secure a six inch (15 cm) thick piece of fiberglass housing insulation to another material using a nail gun. If this is attempted when the fiberglass is uncompressed, when the nail is ejected, it will pierce the insulation and pass completely through the insulation. However, if the fiberglass insulation is compressed prior to attempting to secure it with a nail gun, this will not occur, and the nail will be capable of securing the insulation.

The compliant material 120 preferably has certain characteristics. The compliant material 120 is preferably less compressible than the materials to be bonded, and more compressible than the surface 115 of the patterned roll 110. Therefore, the compliant material 120 should preferably have a hardness of less than that of the surface 115 of the patterned roll 110. Preferably, the compliant material 120 has a hardness (which is measured using a durometer) of between about 50 on the Shore A scale to about 62 on the Rockwell C scale, more preferably has a hardness of between about 50 to about 100 on the Shore A scale, and most preferably has a hardness of about 90 on the Shore A scale. (A hardness of 62 on the Rockwell C scale is the hardness of the D2 steel comprising the surface 115 of patterned roll 110.) (While the surface of the anvil roll can have any suitable hardness, the surface of the anvil roll 112 preferably has a hardness that is equal to or greater than that of the patterned roll 110.) The complaint material 120 can comprise any suitable type of material. Suitable materials include brass, rubber, and polymeric materials such as polyurethane. In a particularly preferred embodiment, the compliant material 120 comprises polyurethane.

The compliant material 120 is preferably wider in width than the materials to be bonded. This allows it to equalize the pressure over the entirety of the materials to be bonded. The compliant material 120 can have any suitable caliper. Preferably, the caliper of the compliant material 120 is great enough to have some appreciable effect on avoiding the problem of punching holes through the cover material 24. The caliper of the compliant material 120 is preferably no greater than the height of the pattern elements 116. The pattern elements may, for example, have a height of about 2 mm. In one non-limiting embodiment, it has been found that a compliant polyurethane material having a hardness of about 90A on the Shore A scale which has a height of about 1.5 mm is suitable.

The compliant material 120 is preferably adhered to the surface 115 of the patterned roll. The complaint material 120 can be adhered to the patterned roll 110 in any suitable manner, such as by welding, or by adhesives.

The purpose of the load bearing members 122 is to balance the patterned roll 110 (that is, to equalize the forces on the patterned roll 110 when the materials to be bonded pass between the patterned roll 110 and the anvil roll 112). The use of the load bearing members 122 is particularly preferred when the pattern on the patterned roll 110 is "unbalanced" or "imbalanced." By "unbalanced" or "imbalanced", it is meant that the pattern elements 116 are distributed in a manner in which the pressure in the nip 114 between the patterned roll 110 and the anvil roll 112 varies around the circumference of the patterned roll 110 due to differences in the surface area of the lands 118 of the pattern elements 116 and/or due to the distribution of the pattern elements 116.

The load bearing members 122 can be omitted when the bonding pattern is balanced. However, as will be discussed in greater detail below, it may be desirable to use load bearing members 122 even when the bonding pattern is balanced to provide greater flexibility in using pattern elements 116 that have a greater height.

The load bearing members 122 may be in any suitable configuration. The load bearing members 122 may be in the form of continuous rings around the patterned roll 110. It also possible for the load bearing members 122 to be in the form of intermittent elements. If the load bearing members 122 are in the form of intermittent elements, however, they are preferably in an arrangement that is staggered around the circumference of the patterned roll 110 in such a manner that they effectively form a continuous ring around the circumference of the patterned roll 110. As shown in FIG. 12, the load bearing members 122 are preferably in the form of continuous rings around the patterned roll 110.

In the embodiment shown in the drawings, the load bearing members 122 are preferably located adjacent to each side edge of the patterned roll 110. The load bearing members are preferably located laterally outboard of the portion of the surface 115 of the patterned roll 110 along which the materials to be bonded will contact (that is, they are preferably located between the central portion of the patterned roll 110 and the side edges of the patterned roll 110). This ensures that the anvil roll 112 will be capable of making direct contact with the load bearing members 122. It is believed that this contact will even occur when the materials to be bonded are fed into the nip 114 between the rolls. This contact is believed to occur due to the compression of the materials to be bonded in the nip 114 and deformation of the rolls under the high forces that are being applied to bias the rolls toward each other.

Figure 11:
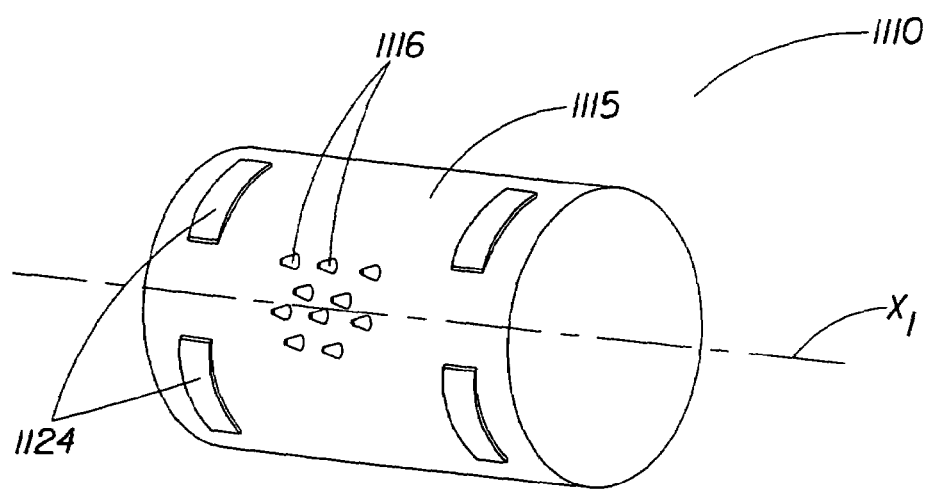
FIG. 11 is a perspective view showing the surface of a prior dynamic bonding roll with intermittent load bearing members thereon.

A comparison of FIGS. 11 and 12 shows the manner in which the load bearing members 122 are believed to function in greater detail. FIG. 11 shows an example of a patterned roll 1110 which does not have bearing members of the type described herein. The distribution of pattern elements 1116 on the patterned roll 1110 is both "nested" and balanced. The term "nested" as used herein refers to distributions of pattern elements 1116 that exhibit a degree of overlap as one looks at the pattern proceeding around the circumference of the patterned roll 1110. This ensures that the anvil roll 1112 will be continuously riding over the tops of the pattern elements 1116 in the nip area 1114, and will not drop or dip down between each pattern element 1116. If the pattern elements 1116 were not nested, and the anvil roll 1112 did dip down between pattern elements 1116, the rolls, which are being held closely together at very high pressures and are rotating at high speeds, would operate in an extremely rough manner, akin to a flat tire on an automobile.

In the roll 1110 shown in FIG. 11, there are identical groups of pattern elements similar to the group shown on other parts of the roll. There are also bearers or bearer strips 1124 between the groups of pattern elements. The other identical groups of pattern elements cannot be seen in FIG. 11 since only a portion of the surface of the roll is shown. However, the single group of pattern elements and the bearers 1124 are shown sufficiently to describe the concept in issue. As shown in FIG. 11, when the pattern is balanced, any bearers or bearing strips 1124 need only be provided in a non-continuous (or intermittent) arrangement around the circumference of the patterned roll 1110. The bearers 1124 are provided in those locations where no pattern elements 1116 are present. This is because the total force from the loading mechanism is transferred from the pattern elements to the bearers 1124 when the patterned roll 1110 rotates. Balanced patterns are required, meaning that the bonding area in the nip (that is, the surface area of the portions of the rolls which are in contact within the nip) at any point around the roll must remain constant. If it were allowed to vary, the bonding pressure would also vary and inconsistent bonds would result.

FIG. 12 shows an example of a patterned roll 110 that can be used in embodiments of the method described herein which have a non-nested and an imbalanced pattern of pattern elements 116 thereon. Although only a portion of the roll 110 with a single group of pattern elements 116 is shown in FIG. 12, the patterned roll 110 preferably comprises several similar patterns of dots spaced around the circumference of the roll 110. (By "dots", it is meant that the pattern elements have circular land areas.) Each group of dots is distributed in the desired arrangement to form bonds on the product in issue. For example, to bond the tube forming composite web shown in FIG. 8, each group of dots may be arranged in a linear pattern of three dots. To bond the interlabial device 1020 shown in FIG. 15, each group of dots may be in a semi-circular arrangement of four or five dots as in the case of the group of pattern elements shown in FIG. 16.

For purposes of this discussion, it will be assumed that there are six groups of dots around the circumference of the roll 110. All of the pattern elements 116 in this example are of the same height. Three of the dot patterns have pattern elements 116 with lands defining a circular bonding surface having a diameter of 2 mm. The other three dot patterns have pattern elements 116 with a circular bonding surface having a diameter of 3 mm. The groups of pattern elements 116 alternate around the surface of the patterned roll 110 with each group of 3 mm diameter pattern elements following a group of 2 mm diameter pattern elements.

There was no convenient way known to the inventors to form bonds using both the 2 mm diameter pattern elements and the 3 mm diameter pattern elements, prior to the invention of the bearing members 122 described herein. For example, using a conventional roll arrangement, it was possible to form bonds with the 2 mm diameter elements, but not with the 3 mm diameter elements. If the proper pressure was selected to form bonds with the 2 mm diameter elements, there would not be sufficient pressure to form bonds using the 3 mm diameter elements. The opposite was also true (it was possible to form bonds with the 3 mm diameter elements, but not with the 2 mm diameter elements). If the proper pressure was selected to form bonds with the 3 mm diameter elements, the pressures would be too high for bonding with the 2 mm diameter elements, and holes be punched through the materials to be bonded.

The bearing members 122 described herein were then developed. As described above, the bearing members 122 are preferably provided in the form of continuous rings around the circumference of the patterned roll 110. To ensure dynamic balancing of the patterned roll 110, an amount of material equal to the surface area of the pattern element is removed from the bearing members. As shown in FIG. 12, the bearing members 122 preferably have small cut out areas 126 on each side. The cut out areas 126 are preferably located along the same longitudinal axis on the surface of the roll on which the pattern elements 116 are located. There are two cut out areas 126 for each pattern element 116. The cut out areas 126 shown in FIG. 12 are each semi-circular in shape. The size of each of the cut out areas 126 is preferably equal to one-half the size of the surface of the pattern elements 116 that are located on the common longitudinal axis.

The bearing members 122 should have a hardness of greater than or equal to the surface of the patterned roll 110 and the pattern elements 116. The bearing members 122 can comprise any suitable type of material. The bearing members 122, like the surface of the patterned roll 110 and the pattern elements 116, are preferably comprised of D2 steel.

The bearing members 122 may have a caliper that is less than, greater than, or equal to the height of the pattern elements 116. Preferably, to simplify the process set up, the caliper of the bearing members 122 is the same as the height of the pattern elements 116. The pattern elements 116 may, for example, have a height of about 2 mm. In one non-limiting embodiment, it has been found that bearing members 122 also having a height of about 2 mm is suitable. The bearing members 122 can be of any suitable width. The bearing members 122 are preferably of a width that provides them with a surface area along each portion of a longitudinally oriented zone taken along the surface of the patterned roll 110 (that is, oriented parallel to the axis of the roll) which is equal to or greater than that of the total surface area of the lands 118 on the pattern elements 116 that lie within the same zone. In the embodiment shown in FIG. 12, the bearing members 122 have a width of about 6 mm (as measured through a portion of the bearing members 122 that does not include the cut out areas 126).

The bearing members 122 can be integrally formed on the patterned roll 110, or they can comprise separate elements that are adhered to the surface 115 of the patterned roll 110. The bearing members 122 are preferably integrally formed on the surface 115 of the patterned roll 110. If the bearing members 122 are adhered to the patterned roll 110, they can be adhered in any suitable manner, such as by welding.

Without wishing to be bound by any particular theory, it is believed that the bearing members 122 allow for bonding using unbalanced patterns because the pressure in the bonding area is no longer solely a function of the surface area of the pattern elements or a function of the presence or absence of the pattern elements. With the bearing members 122, the pressure in the bonding area becomes controlled by the material properties of the rolls, particularly the patterned roll 110, and the materials to be bonded, as well as the geometry (that is, the height and surface area) of the pattern elements 116 and the bearing members 122. It is believed that as bonding takes place under the relatively high pressures used, there is deformation of the rolls, particularly of the pattern elements 116. The pressure in the bonding area is believed to result in a compressive deflection in the pattern elements 116. The pressure in the bonding area may also result in a degree of deflection in the surface of the patterned roll 110 around the base of the pattern elements. Localized deformation on the anvil roll 112 at the location of the points of contact with the pattern elements 116 is also possible.

It is believed that the magnitude of the deformations in the pattern elements 116 and the surrounding areas is on the order of the thickness of the bonds formed by this process. In the embodiment described herein, the bonds have a thickness in the range of about 0.0015 to about 0.002 inches (about 0.038 mm to about 0.05 mm). This deformation allows the anvil roll 112 to maintain constant contact with the bearing members 122, even in the areas where there are pattern elements 116 present and the intervening materials to be bonded are being fed into the nip 114 between the patterned roll 110 and the anvil roll 112. For this to be possible, the loading force must be sufficiently high to ensure constant contact between the bearing members 122 and the anvil roll 112. The bearing members 122, thus act as a "stop" for the anvil roll 112 to prevent further compressive deflection of the pattern elements 116.

The bearing members 122 can be designed to be sufficiently strong so that once the anvil roll 112 is in contact with the bearing members 122, no further increase in the bonding pressure on the pattern elements 116 would be possible. If the loading force were to increase, only the load acting on the bearing members 122 would increase, assuming they were very rigid.

The balancing of the patterned roll 110 has particularly important implications. This aspect of the bonding method can be used to produce bonding patterns with pattern elements having different size lands around the circumference of the patterned roll. This aspect of the bonding method can also be used to that are not subject to the previous mechanical limitations. The bond patterns do not have to have nested pattern elements, and the bond patterns do not have to be balanced. For example, in prior bonding processes, creation of complex patterns, such as a pattern like that shown in FIG. 17, which is nested and balanced, involves an extremely complicated designing process. The balancing of the patterned roll eliminates the need to go through complex design work to assure that the bond pattern is nested and balanced.

In addition, bonding patterns can be created which are tailored to suit some particular bonding need, or to suit consumer preference, rather than process limitations. In addition, the method described herein can be used to create an unlimited number of bond designs for aesthetic purposes or for other purposes. For example, using the techniques described herein could be used to write a script or emboss a picture into the materials to be bonded.

Further, the use of the bearing members 122 in the method permits pattern elements 116 having much greater heights to be used. Previous pattern elements were typically about 0.015 inches (about 0.38 mm) in height. As discussed herein, the pattern elements 116 can range in height up to 2 mm, or more. This allows thicker materials to be bonded. Providing a patterned roll with pattern elements having a greater height, however, is not limited to use in bonding thick materials. It also can be used to bond through thin materials because the bearing members 122 will keep the pattern elements 116 from puncturing the materials to be bonded.

This aspect of the method is also believed to result in increased life of the patterned roll 110. Generally, relief patterned rolls wear out because of stresses on the pattern elements. The use of the bearing members is believed to reduce stresses by bearing a portion of these stresses and relieving the pressure on the pattern elements. As discussed above, the bearing members may also act as a "stop" to prevent further compressive deflection of the pattern elements. It is believed, that because the bearing members may act as a "stop" to prevent further compressive deflection of the pattern elements, the pattern elements will not be strained beyond their plastic deformation point.

Preferred Embodiments for Bonding and/or Embossing

It has been surprisingly discovered by the Applicants that when the height of the continuous load bearing members is greater then the height of the pattern elements and when the load bearing members are subjected to a compression state, the above described "balancing" of the pattern elements of the pattern roll becomes not necessary. The elimination of the "balancing" not only provides substantial cost savings in fabricating the bonding apparatus of the present invention, but also eliminates limitations in designing bonding patterns, thus, providing greater opportunities in product design utilizing fusion bonding.

It has been further surprisingly discovered by the Applicants that the preferred embodiments described below can bond laminates having greater differences in material thickness or caliber, thus, providing opportunities for utilizing a wider range of materials. Further, the preferred embodiments can tolerate greater variations in the area of the land surfaces of the pattern elements, thus, again broadening the design options for the bonding patterns and product design. Further, the preferred embodiments can also improve the longevity of the pattern elements, resulting in additional cost benefits associated with fabrication and operation of the methods of the present invention. Further, the preferred embodiments can tolerate pattern elements having a greater height, thus, providing opportunities for bonding thicker laminates. Further, the preferred embodiments can bond at lower velocities, thus, broadening the operation window. Further, the preferred embodiments provide a lower-noise bonding operation, especially at lower velocities. Still further, the preferred embodiments can be used for bonding and/or embossing of laminates including only bondable materials or both bondable and incompatible materials.

Figure 12C:
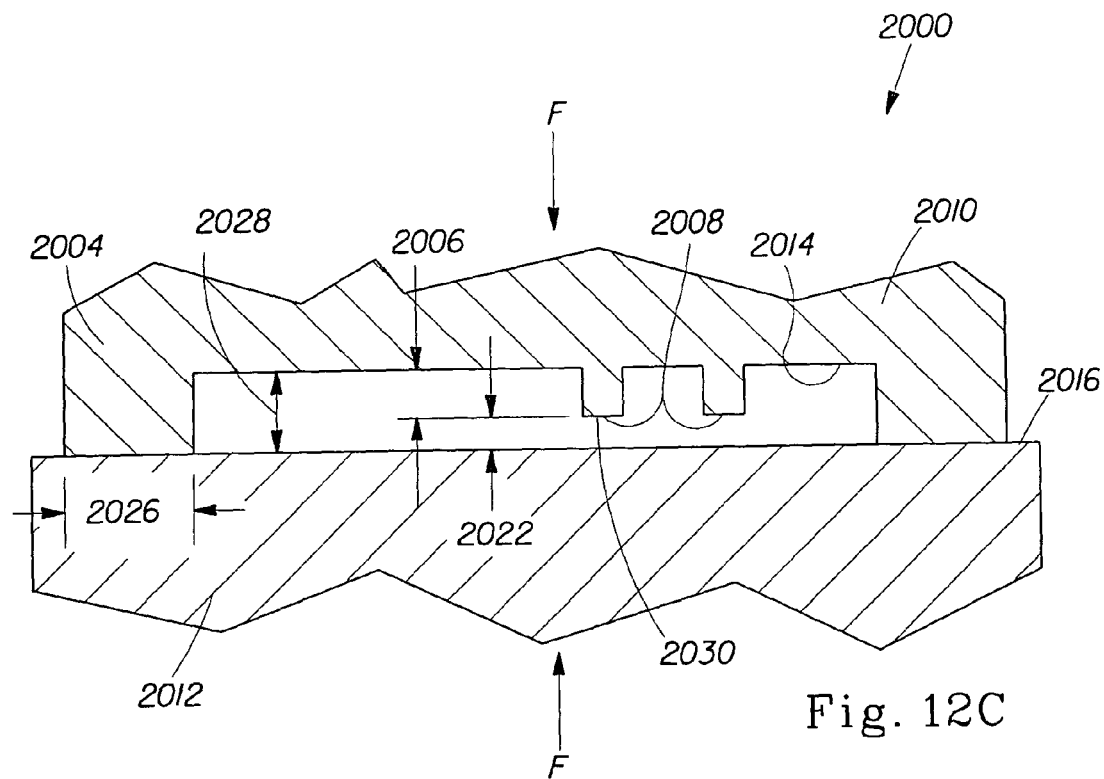
FIG. 12C is a schematic cross-section view of the apparatus of FIG. 12B taken across line 12C—12C.
Figure 12D:
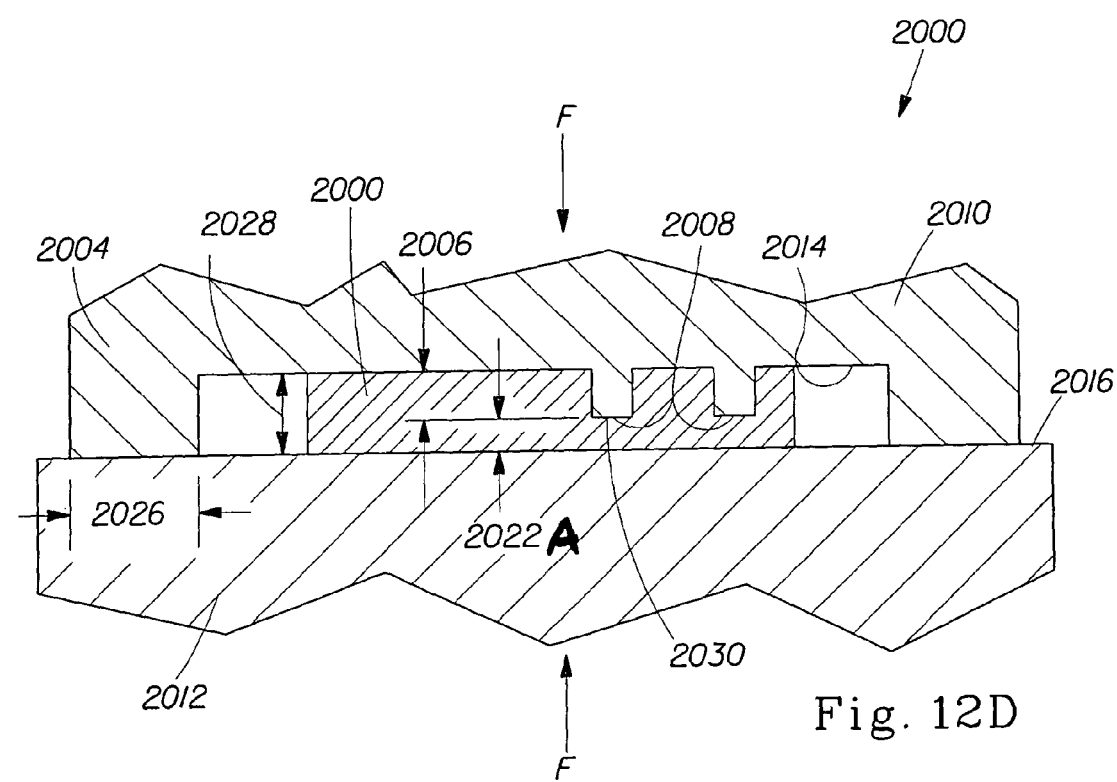
FIG. 12D is a schematic cross-section view of the first preferred embodiment with a laminate in the nip area between the rolls and the rolls being under a sufficient load force F.

FIGS. 12A, 12B, 12C, and 12D show a first preferred embodiment 2000 of the methods and the apparatus of the present invention, wherein the height 2002 of the continuous load bearer members 2004 is greater than the height 2006 of the pattern elements 2008. FIG. 12A is a schematic front elevation view of the first preferred embodiment 2000 when the load force F is low or zero and when there is on laminate yet in the nip area between the rolls. FIG. 12B is a schematic side elevation view of the first preferred embodiment 2000 of FIG. 12A when the load force F is sufficient to compress the load bearer members 2004 and when there is no laminate in the nip area between the rolls. FIG. 12C is a schematic cross-section view taken along line 12C—12C of FIG. 12B, the roll area is under a sufficient load force F and there is no laminate between the rolls. FIG. 12D is a schematic cross-section view of the first embodiment 2000 with a laminate in the nip area between the rolls and the rolls being under a sufficient load force F.

Referring to FIGS. 12A, 12B, 12C, and 12D, the first preferred embodiment 2000 includes a pattern roll 2010 and an anvil roll 2012. Both rolls 2010 and 2012 have an outer diameter of about 130 mm; however, the rolls can have any suitable diameter or different diameters. The rolls 2010 and 2012 are capable of counter-rotating in relation to each other. The pattern roll 2010 has an outer surface 2014 and at least one or a multiplicity of pattern elements 2008 extending from the outer surface 2014 at a pattern element height 2006. The pattern elements 2008 can have straight or angled side walls as described herein.

The anvil roll 2012 has an outer surface 2016. Between the outer surface 2016 of the anvil roll 2012 and the outer surface 2014 of the pattern roll 2010 there are two load bearer members 2004 having a bearer height 2002. The bearer height 2002 is greater than the pattern height 2006.

The pattern roll 2010 and the anvil roll 2012 are always in contact with each other through the load bearer members 2004 under the load force F. The load bearer members 2004 can have suitable alternative embodiments. For example, the load bearer members 2004 can be separate elements from the rolls 2010 and 2012, disposed between the outer surfaces of the rolls. Alternatively, they can be integral with the outer surface 2014 of the pattern roll 2010 (as shown in FIGS. 12A, 12B, and 12C) or they can be integral with the outer surface 2016 of the anvil roll 2012. Further, the load bearer members 2004 can be any combination of the above alternatives.

The number of the load bearer members can vary. In the first preferred embodiment 2000, there are two load bearer members 2004 disposed at the both ends of a bonding pattern 2024. However, the methods of the present invention can have a single load bearer member or more than two load bearer members.

The pattern roll 2010, the anvil roll 2012, and the bearer members 2004 are preferably made of a steel; however, any suitable material can be applicable with the methods of the present invention.

When there is no laminate between the rolls and when the load force F is sufficiently low or zero, there is a no-load gap 2018 (FIG. 12A) in the nip area between the pattern element 2008 and the outer surface 2016 of the anvil roll 2012. The no-load gap 2018 is generally equal to the difference between the height 2002 of the load bearer member 2004 and the height 2006 of the pattern element 2008.

However, when the load force F is sufficient to compress the height 2002 of the load bearer members 2004 at a compression distance 2020 (FIG. 12B), the no-load gap 2018 is reduced to a static load gap 2020, again when there is no laminate between the rolls. (FIG. 12C). The static load gap 2020 is a gap in the nip area, measured between the pattern element 2008 and the outer surface 2016 of the anvil roll 2012, when a sufficient compression force F is applied to reduce the no-load gap 2018 and when there is no laminate in the nip area between the rolls.

In the first preferred embodiment 2000 of the present invention, the no-load gap 2018 (FIG. 12A) is about 0.076 mm (0.0030 inch), which under the compression force F of about 13400 newton is reduced at a compression distance 2020 of 0.013 mm (0.0005 inch) (see FIG. 12B) to the static load gap 2022 (FIG. 12C) of about 0.063 mm (0.0025 inch). Further, preferred dimensions of the embodiment 2000 include a bearer member width 2026 of about 2.0 mm, the bearer member height 2028 of about 2.000 mm, and the pattern element height 2006 of about 1.924 mm, thus, resulting in the no-load gap 2018 of about 0.076 mm. The above force F of about 13400 newton can be provided, for example, by two 8-inch-diameter air bags (203 mm) at a pressure of about 30 pounds per square inch (206842 pascal).

However, it should be noted that the above dimensions of the first preferred embodiment 2000 can vary without departing from the spirit of the present invention. For example, the bearer member width 2026 can vary as desired, requiring a greater forces F for compressing a wider width bearer member and a lower force F for compressing a narrow width bearer member. The force F can also vary depending on the compressibility of the material used for the load bearer member 2004, requiring less force F for more compressible materials.

Referring to FIG. 12C, the height 2006 of the pattern elements 2008 terminates at a land surface 2030 which forms the no-load gap 2018 (FIG. 12A) and the static load gap 2022 (FIG. 12C) with the outer surface 2016 of the anvil roll 2012. The land surface 2030 can vary in shape and in the surface area. For example, the land surface 2030 can be of any desired shape: a circle, an ellipse, an oval, a triangle, a square, a rectangle, an elongated rectangle, a polygonal, or any combination thereof. As noted herein, the preferred embodiments 2000 and 2100 of the methods of the present invention can tolerate substantially greater variations in the area of the land surfaces of the pattern elements. For example, it has been surprisingly discovered by the Applicants that the area of the land surface 2030 can range from about 2 mm² to at least about 80 mm².

Figure 12E:
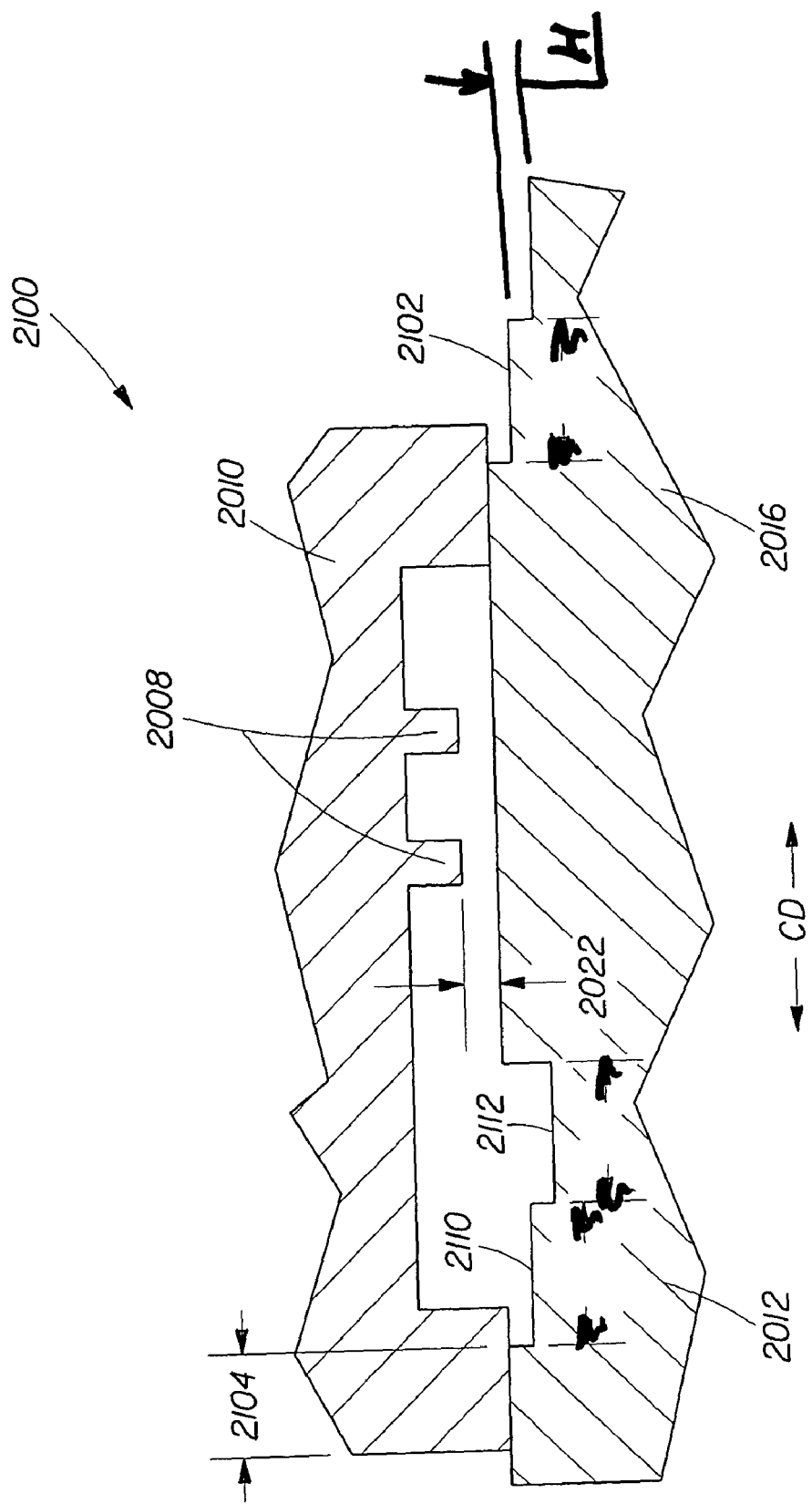
FIG. 12E is a schematic cross-section view of another preferred embodiment of the present invention having a stepped outer surface of the anvil roll.

FIG. 12E is a cross-section view of a second preferred embodiment 2100 of the present invention, having a stepped outer surface 2102 of the anvil roll 2106. The embodiment 2100 provides adjustable parameters of the methods of the present invention. For example, the effective width 2104 of the load bearer members 2004 can be changed by moving the pattern roll 2010 or the stepped anvil roll 2106 in relation to each other in a cross-machine direction CD. Further, the stepped outer surface 2102 of the anvil roll 2106 also provides an adjustable no-load gap 2108 (and, consequently, an adjustable static load gap) by moving the pattern roll 2010 or the stepped anvil roll 2106 in relation to each other in the cross-machine direction CD such that the load bearer members 2004 are in contact with steps 2110 or 2112. The height of the steps 2110 and 2112 can vary as desired, and the number of steps 2110 and 2112 can also vary as desired, without departing from the spirit of the present invention. For example, in the second preferred embodiment 2100, the height H of each of the steps 2110 and 2112 is about 0.025 mm (0.001 inch) and the number of steps is two. Accordingly, the steps 2110 and 2112 can provide at least two additional variations of the no-load gap 2108 of about 0.051 mm (0.002 inch) and about 0.025 mm (0.001 inch), respectively.

In the above preferred embodiments of the present invention, a laminate 2200 is provided in the nip area between the outer surfaces of the rotating rolls as shown in FIGS. 12C and 12D, and the rolls are subjected to a sufficient load force F to provide compression state of the bearer member and the laminate 2200, and to effect a dynamic-load gap 2022A. The anvil roll 2012 can rotate at a tangential velocity $V_A$, which is a tangential velocity of the outer surface 2016 contacting the load bearers 2004. The load bearers 2004 can rotate at a liner velocity $V_B$, which is preferably equal to the tangential velocity $V_A$. However, it should be noted that the tangential velocities $V_A$ and $V_B$ can vary in relation to each other without departing from the spirit of the present invention. Further, the linear velocity $V_L$ of the laminate 2200 can also vary. The velocities $V_A$ and $V_B$ can range from about 60 meters per minute to at least bout 750 meters per minute.

(2) Non-Limiting Variations of the Bonding Process.

There are many possible variations of the bonding process described herein. A non-limiting number of these variations are set out below.

For example, the methods described herein are not limited to use in bonding materials for use in absorbent articles. The methods described herein, may for instance, be used to bond materials for use in making packages, or any other types of articles, particularly where incompatible materials, polymeric materials, or the like are used. In addition, the center laminae of the materials to be bonded does not have to comprise an incompatible material. It can comprise any suitable type of material, including, but not limited to a thermoplastic material.

In addition, the methods of bonding described herein are not limited to the arrangement of rolls shown in the drawings. In other embodiments, for example, both of the rolls can be provided with pattern elements. In embodiments where both of the rolls are provided with pattern elements, the pattern elements can be arranged to make contact with each other. Alternatively, the pattern elements on one of the rolls can be arranged to make contact with the surface of the opposite roll at locations between the pattern elements on the surface of the other roll. In addition, the load bearing members are not limited to being positioned only on the patterned roll. The load bearing members can be provided on the anvil roll, or on both the patterned roll and the anvil roll.

Numerous variations of the bearing members are also possible. For example, it is possible that the bearing members can have at least some portions that are not continuous, and the patterned roll may still provide some or all of the benefits described herein. In addition, the shape of the cut out areas in the bearing members need not be the same as one half of the shape of the pattern elements.

The preferred methods of dynamically bonding these materials may further comprise the step of heating one or both of the rolls. If the rolls are heated, they are preferably heated to a surface temperature that is a predetermined number of degrees below the melting temperature of the thermoplastic material in the cover material.

In other embodiments, the materials to be bonded can be compressed (or "pre-compressed") before they are fed into the nip for bonding. For example, the materials to be bonded can be fed through a pressurized nip between another pair of rolls prior to the set of rolls to pre-compress the materials to be bonded. The pre-compression may involve compressing the entirety of the materials to be bonded, or it may comprise a localized compression in those areas of the tube forming composite web at which the bonds will be formed.

The pre-compression step can also occur in conjunction with the bonding in other types of bonding processes. For example, if ultrasonics are used, the ultrasonic welder or "staker" will generally cause the material to be bonded undergo a degree of compression for the dwell time needed to form the ultrasonic bond. Thus, in the case of conventional ultrasonic welding, a pre-compression step that is separate from the bonding process generally used, is not required.

In addition, for simplicity and clarity of the invention, the apparatus used in the bonding process is described herein as comprising a set of rolls. However, rolls are but exemplary nip defining members. Accordingly, it is not intended to thereby limit the present invention to an apparatus comprising rolls per se. In the same vein, use of the term "pattern element" is not intended to limit the methods described to bonding patterns consisting of only discrete, spaced pattern elements to the exclusion of other patterns: e.g., reticulated patterns or patterns comprising continuous or elongate lines of bonding.

The methods described herein can further comprise any of the process limitations or steps described in U.S. Pat. No. 4,854,984 issued to Ball, et al on Aug. 8, 1989.

Another factor that should be taken into consideration, in some embodiments of the present invention, when forming bonds using a dynamic bonding process is evenly distributing the load on the pattern elements. This is most significant when a single bonding roll or surface is used to bond a material having portions with different thicknesses. The different thicknesses may occur in several different situations. For example, the material to be bonded could be profiled or calendered so that it has regions with different thicknesses. Alternatively, the material to be bonded may comprise a laminate wherein the length and/or width of all the layers is not the same. In such a case, some of the bonds may have to pass through more layers than the other bonds.

One way of evenly distributing the load on the pattern elements in such situations, is to vary the angle of the side walls 119 of the pattern elements 116. The angle of the side walls 119 of the pattern elements 116 that will be penetrating the portions of the material or materials to be bonded which have a greater thickness should be greater than that of the pattern elements 116 that will be penetrating the portions of the material(s) which have a lesser thickness. For example, the angle of the side walls 119 of the pattern elements 116 that will be penetrating the thinner portions of the material(s) to be bonded may form an angle of about 50°, and the angle of the side walls 119 of the pattern elements 116 that will be penetrating the thicker portions of the material(s) to be bonded may be about 70°. The pattern elements 116 that will be penetrating the thicker portions of the material(s) to be bonded may also have a greater height, if desired (or the other pattern elements can be made shorter).

As discussed above, the methods of the present invention can be carried out using adhesives, cohesives, hydrogen bonding (for example, if one of the materials to be bonded comprises cellulose), heat and/or pressure, or ultrasonics. Preferably, however, either the dynamic bonding process or ultrasonics are used. Such processes are particularly preferred if the bondable material, such as second web of material 24 is treated by a chemical or composition that interferes with usual bonding methods (particularly adhesives). For example, these bonding processes would be preferred if the second material is treated with a skin care composition, or a material that alters the hydrophilicity of the second material.

Examples of the latter types of surface treatments are described in P&G U.S. Pat. No. 5,693,037 entitled "Absorbent Articles Having Improved Surfactant-Treated Hydrophilic Topsheets", issued to Yan-Per Lee, et al. on Dec. 2, 1997. The dynamic bonding process and the ultrasonic bonding processes described herein are capable of either bonding through such treatments, or transferring enough heat through such coatings or surface treatments that the bond can be formed with the underlying material. Alternatively, if such surface treatments are intermittently applied, the pattern on the bonding device may be designed so that the bonds penetrate the untreated portions of the material.

FIG. 7 shows that the bonding compresses, or more preferably, displaces the compressible foam absorbent material 22 in localized areas where the bonds 94 are formed. This isolates a three-dimensionally shaped portion 100 of the tube forming composite web 88 from the remainder of the tube forming composite web 102 and forms the isolated portion 100 (as well as the entire tube forming composite web 88) into a distinct shape. The tube forming composite web 88 is shaped, preferably symmetrically, on both sides. This is possible because the bonding exerts pressure on only a portion of the tube forming composite web 88 where the tube forming composite web 88 is compressed by the pattern elements 116 against the curved surface of the anvil roll. This embodiment of the methods of the present invention, thus, differs from embossing processes which would create a structure with one embossed side and one flat side.

D. Attaching The Tube of Absorbent Material To A Base Pad To Form A Compound Sanitary Napkin.

After the bonding process, the bonded tube forming composite web 88 is preferably cut into a plurality of individual tubes of absorbent material, each of which will be placed on top of a base pad to form a compound sanitary napkin.

As shown in FIG. 8, the apparatus used for cutting the bonded tube forming composite web 88 comprises a pair of rolls 130 and 132. One of the rolls, roll 130, has at least one, and preferably a plurality of knife elements 134 on its surface. The knife elements 134 are preferably configured to make a continuous, generally transverse direction cut in the continuous bonded tube forming composite web 88. The other roll 132 serves as an anvil member, and, thus, may be referred to as anvil roll 132. The knife roll 130 and anvil roll 132 also define a nip 136 therebetween. After the cutting step, the individual tube of absorbent material 88 which are sent to a conveyor 140 for attachment to the base pad to form a compound sanitary napkin.

In the case of the individual tube of absorbent material shown in FIG. 7, the remainder 102 of the tube forming composite web 88, which is not held together by bonds, is unfolded and spread out prior to attachment of the tube forming composite web 88 to the base pad. The bonding and the unfolding of the remainder 102 of the tube forming composite web 88 forms the tube forming composite web 88 into a profiled shape in which the portion of the tube forming composite web 88 that will form the top of the absorbent tube on the finished product, is given a narrower width. Preferably, as shown in FIG. 13, the portion of the composite web 88 that will form the top of the absorbent tube on the finished product defines a ridge 106 that projects perpendicularly from the top of the remainder of the forming composite tube 102 (and the remainder of the sanitary napkin). As shown in FIG. 13, the bonding also provides the tube forming composite web 88 with a quilt-like pattern where the tube forming composite web 88 is puckered around the bond sites 94.

FIG. 13 shows a compound sanitary napkin 800 having the tube of absorbent material 88 on the body-facing side thereof, which was bonded by the methods of the present invention.

To form the compound sanitary napkin 800, a sanitary napkin can serve as the panty protector (or "base pad") 820 and the tube of absorbent material 88, which will serve as the primary menstrual pad is placed on top of the base pad 820 and attached thereto at least at its ends. Sanitary napkins suitable for use as the base pad 820 include ALWAYS ULTRA sanitary napkins marketed by The Procter & Gamble Company of Cincinnati, Ohio.

In a particularly preferred embodiment, the base pad 820 comprises a variation of such an ALWAYS ULTRA sanitary napkin which has an absorbent core comprising a tissue laminate with superabsorbent hydrogel-forming material particles therebetween, and a tissue and a DRI-WEAVE apertured film overlying the absorbent core. Suitable tissues are manufactured by Merfin Hygienic Products. The tissue overlying the absorbent core is preferably joined to the absorbent core by a spiral pattern of adhesive.

The tube of absorbent material 88 can be joined to the base pad 820 in any suitable manner. The attachment of the tube 88 to the sanitary napkin 820 is preferably achieved by fusion bonding extensions 58 of the topsheet material 56 at the ends of the tube to the base pad 820. In some preferred embodiments of such a compound sanitary napkin, there may also be attachment to the base pad 820 between the ends of the tube of absorbent material 88 and the base pad 820. The tube of the compound sanitary napkin can be attached to the base pad between its ends by any suitable attachment means, such as by adhesives.

The sanitary napkin 800 has a first (or front) end region 828, a second (or rear) end region 830, and a central region 832 positioned between the first and second end regions. As shown in FIG. 13, the tube of absorbent material 88 is profiled from the front end region 828 of the sanitary napkin 800 to the rear end region 830 of the sanitary napkin as a result of the bonding. More specifically, the tube of absorbent material 88 has its highest caliper in the center of the sanitary napkin along the transverse centerline, T, and tapers to a lesser caliper at the ends of the sanitary napkin.

The bond patterns can be varied to create a tube of absorbent material with increased caliper along all or any portion of the length of the sanitary napkin 800. For example, the bonding can be such that the increased caliper is confined to the central region 832 of the sanitary napkin 800. Alternatively, the bond pattern can be used to provide increased caliper in the end regions, or in a portion of central region and a portion of the end regions.

2. Alternative Embodiments of the Methods of the Present Invention

Numerous alternative embodiments of the present invention exist. For example, in one alternative embodiment, the absorbent material in the tube of absorbent material need not be formed into particulate material before it is bonded. That is, a solid piece of absorbent material can be used. However, the bonding through a solid absorbent material, such as an absorbent foam material, may be more difficult, particularly if it is over about 4 mm thick.

It is also possible to bond through other types of materials, such as low density absorbent materials, using the methods of the present invention. For example, the methods of the present invention can be used to bond through non-calendered airfelt. If it is desired that the airfelt be calendered, the airfelt can be calendered after it has been enveloped in the bondable material and bonded according to the methods of the present invention.

The methods of the present invention, however, provide several advantages in comparison to merely embossing an absorbent article, such as an absorbent article comprising an embossed airfelt absorbent core. In such absorbent articles, the topsheet may be adhesively bonded to the airfelt absorbent core. The backsheet may be adhesively bonded to the airfelt as well. The cellulosic fibers in the airfelt are held together by hydrogen bonds. These hydrogen bonds suffer from the disadvantage that they will tend to be released by liquids. Adhesives also suffer from the disadvantage that they may tend to be released by liquids and if certain surface treatments are applied to the components of the absorbent article, such as the topsheet.

Figure 14:
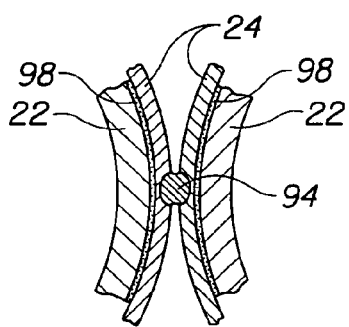
FIG. 14 is a schematic view showing an alternative way of bonding two incompatible materials together using the methods of the present invention.

FIG. 14 shows another use of the methods of the present invention. In the prior embodiments, the methods of the present invention involved placing materials that were capable of being bonded on the outside surfaces of an incompatible material and bonding these materials together by penetrating through the incompatible material. In FIG. 14, the method of the present invention is used to bond two incompatible materials to materials that are capable of being bonded, which lie inside the incompatible materials.

FIG. 14 shows two webs of incompatible material 22. The webs of incompatible material 22 may comprise any of the incompatible materials described herein. Preferably, the webs of incompatible material comprise an absorbent foam material. Although it is difficult to attach such absorbent foam materials to other materials using adhesives, in this embodiment, a layer of adhesive 98 is used to bond each of the webs of absorbent foam material 22 to a web of material 24 that has a higher bondability. This adhesive bond is, however, subject to the risk that the absorbent foam material may separate therefrom due to the low structural integrity of the absorbent foam material. The webs of material 24 having the higher bondability can be any of the second materials described herein. Preferably, the webs of material 24 having the higher bondability comprise nonwoven webs.

As shown in FIG. 14, the webs of absorbent foam material 22, with the nonwoven webs 24 adhesively attached thereto are placed in a face-to-face relationship with the nonwoven webs 24 adjacent to each other. The entire composite structure thus formed is then bonded together by the methods described herein. The composite structure can be bonded by passing it through a nip between a pair of rolls such as those in the apparatus shown in FIG. 8. This will cause a bond 94 to be formed between the two nonwoven webs 24.

The bond 94 in this embodiment, may be a "hidden" bond which is not visible from outside the absorbent foam material 22. The bond 94 may be hidden because that pattern element which formed the bond will typically displace a small amount of the foam material. In addition, after the bonding, the foam material 22 may expand over the bond area to make the places where the foam material was displaced, less visible.

Figure 15:
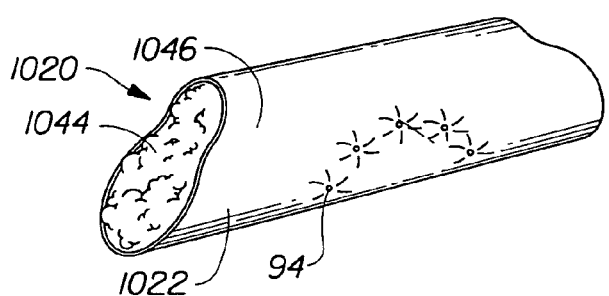
FIG. 15 is a perspective view of an absorbent interlabial device that is bonded and shaped by the methods of the present invention.
Figure 16:
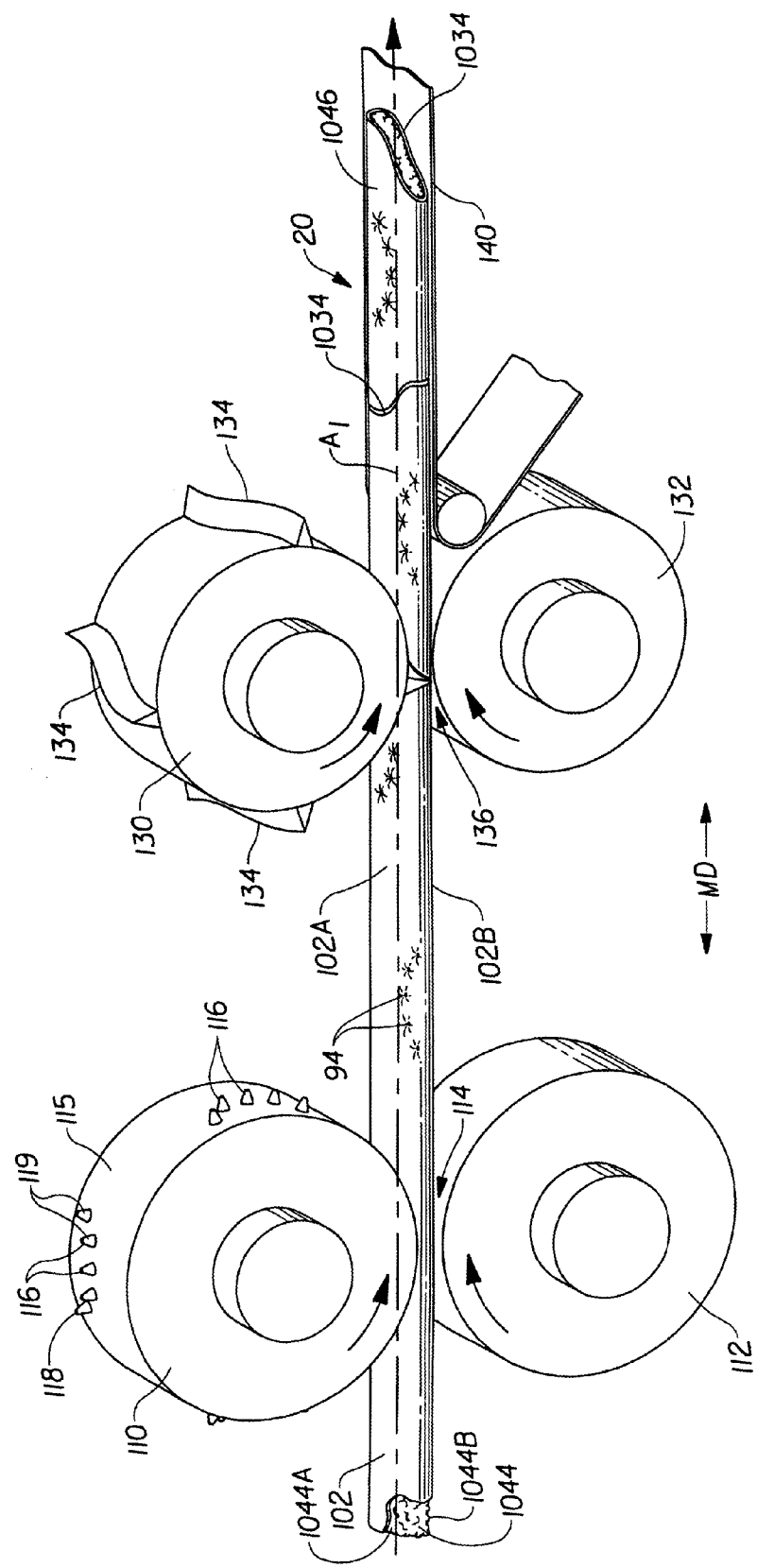
FIG. 16 is a perspective view of a variation of the methods of the present invention which is used to make an interlabial device.

In addition, the methods described herein can be used for other purposes and to make other types of absorbent articles. For instance, FIG. 15 shows an absorbent interlabial device 1020 that is bonded and shaped by the methods of the present invention. The absorbent interlabial device 1020 may comprise any suitable absorbent material, including any of the incompatible materials described herein. In the embodiment shown in FIG. 15, the absorbent interlabial device 1020 comprises a rayon core 1044 that is wrapped with a nonwoven web cover material 1046. Rayon is typically incompatible using conventional bonding techniques. As shown in FIG. 16, however, the methods of the present invention can be used to bond and shape the rayon core 1044 by providing bonds 94 between the nonwoven cover 1046 on opposite sides of the absorbent interlabial device that penetrate the rayon.

As shown in FIG. 16, a first portion 1046A of the cover material 1046 is preferably bonded through the absorbent rayon material 1044 to a second portion 1046 of the cover material. The apparatus used for bonding the covered absorbent material 1044 preferably comprises a pair of cylindrical rolls, patterned roll and anvil roll, 110 and 112. The cylindrical rolls 110 and 112 are similar to those shown in FIG.

8. As in the embodiment shown in FIG. 8, preferably, at least one of the rolls, roll 110, has a relief pattern on its surface. The patterned roll 110 is configured to have a circular cylindrical surface 115, and a plurality of protuberances or pattern elements 116 which extend outwardly from the surface 115. The relief pattern and the land surfaces 118 on the pattern elements 116 can be in any suitable configuration. The side walls 119 of the pattern elements 116 preferably form an angle similar to that described relative to the roll 110 shown in FIG. 8.

The rolls 110 and 112 are preferably operated in a manner that is the same or similar to that described above for the apparatus shown in FIG. 8 (including, but not limited to, ranges of surface velocity differential between the rolls, range of nip pressures between the rolls, optional possibility of heating one or both rolls, and replacement of the rolls by other types of nip defining members.

The relief pattern, in the embodiment of the apparatus shown in FIG. 16, also comprises a plurality of spaced apart pattern elements (or "pattern element segments") 116 having circular land surfaces 118. In the embodiment of the method shown in FIG. 16, however, the pattern elements 116 are arranged in a "half moon" configuration. The pattern elements 116 are provided in an alternating pattern wherein every other application of the bonding pattern, bonds 94 are formed on opposite sides of the longitudinal axis, A1, of the covered "rope" of absorbent material.

The bonding process shown in the drawings penetrates through the sliver of absorbent material 1044 and autogenously bonds the first portion 1046A of the cover material to the second portion 1046B of the cover material 1046.

The embodiments of the absorbent articles shown in the drawings demonstrate other advantages of the methods of the present invention. The bonds 94 can be placed in a virtually unlimited number of patterns. These bonds 94 can be used to create products having a virtually unlimited number of possible geometric shapes. The bonding patterns can also be used to add structural stability as well as shaping the absorbent article by adding a degree of stiffness to the product along a line that passes through the bonds. This line can be rectilinear, curvilinear, or partially rectilinear and partially curvilinear. Deep quilted impressions can be created for liquid handling or appearance. The methods of the present invention can also be used on a manufacturing line running at high speeds (e.g. 700–1,000 feet per minute), and is not limited to particular patterns, as are sewing processes.

Figure 17:
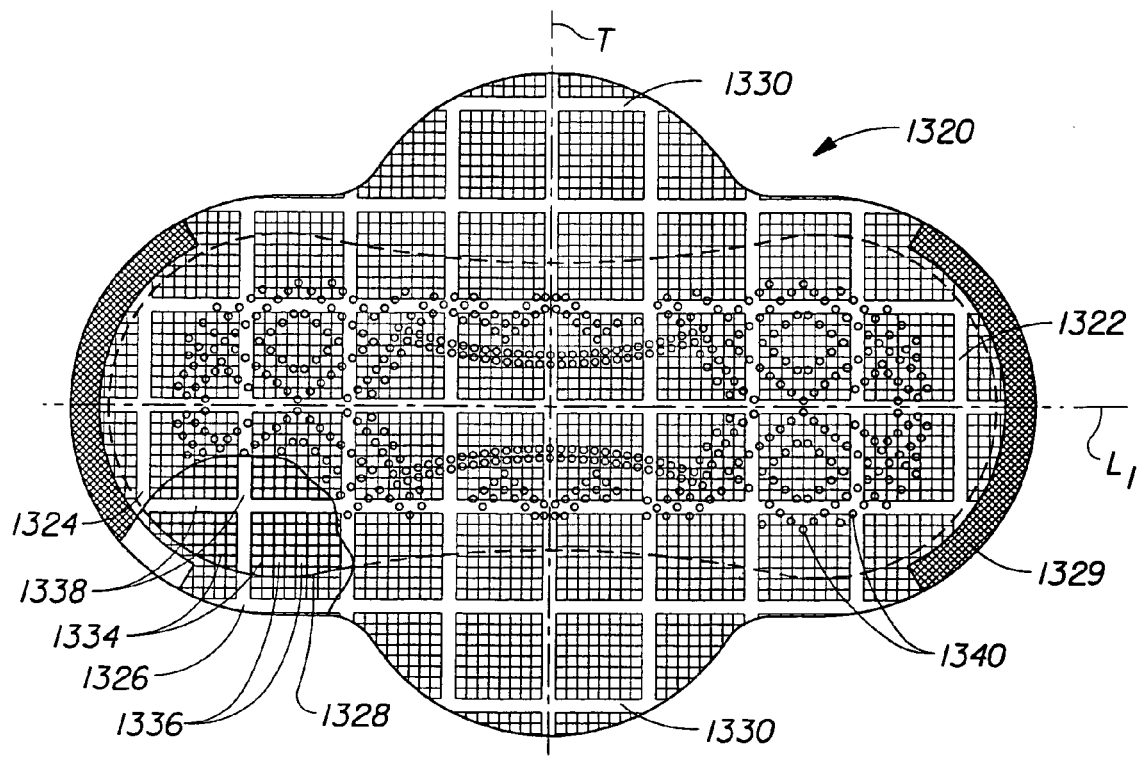
FIG. 17 is a partially fragmented plan view of a sanitary napkin that is made by the methods of the present invention.
Figure 18:
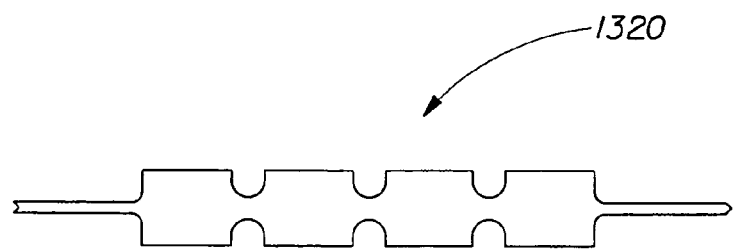
FIG. 18 is a schematic cross section of a portion of the sanitary napkin shown in FIG. 17.

FIGS. 17 and 18 show a sanitary napkin 1320 that can be produced with several different features using the methods of the present invention. FIG. 17 shows an absorbent article (an extensible sanitary napkin designated 1320) in which the method of the present invention was used to simultaneously perform several different operations in the process of making the absorbent article. The sanitary napkin 1320 comprises a main body portion 1322. The main body portion 1322 comprises a liquid pervious topsheet 1324, a liquid impervious backsheet 1326 joined to the topsheet, and an absorbent core 1328 positioned between the topsheet 1324 and the backsheet 1326. These components can be joined in any suitable manner that allows the assembled sanitary napkin 1320 to be extended. The sanitary napkin 1320 may comprise a pair of end seals 1329 that are formed by fusing the topsheet and backsheet together. The sanitary napkin 1320 also has wings or flaps 1330 extending from each longitudinal side edge of the main body portion 1322 thereof.

The sanitary napkin 1320 shown in FIG. 17 has an absorbent core 1328 with regions 1334 that have been formed into particulate material 1336 by the methods described herein. As shown in FIG. 17, the regions 1334 comprising the particulate material are separated by unformed bands 1338 that are oriented in both the longitudinal direction and the transverse direction. In addition, the method of the present invention was preferably also used to form strainable network regions into the topsheet 1324 and the backsheet 1326. The term "strainable network region" is described in greater detail in U.S. Pat. No. 5,518,801 entitled Web Materials Exhibiting Elastic-Like Behavior, which issued to Chappell, et al. on May 21, 1996. The formation of the strainable network regions into the topsheet 1324 and backsheet 1326 provides these components of the sanitary napkin with extensibility. The unformed bands of the strainable network in the topsheet 1324 and backsheet 1326 provide these extensible components with elastic-like properties. The formation of the absorbent core 1328 into particulate material places the absorbent core 1328 into a form that will not interfere with the extensibility of the topsheet 1324 and backsheet 1326.

The topsheet 1324 and backsheet 1326 can be provided with extensibility in one direction, in more than one direction, or in all directions in the X-Y plane, depending on the pattern of the strainable network formed therein. In the embodiment shown in FIG. 17, the sanitary napkin 1320 is extensible in both the longitudinal and transverse directions. The sanitary napkin 1320 shown in FIG. 17 is preferably extensible in the amounts specified in the disclosure of U.S. Pat. No. 5,611,790 entitled "Stretchable Absorbent Articles", which issued to Osborn, et al. on Mar. 18, 1997.

FIG. 17 shows that the methods described herein can also be used to provide the wings or flaps 1330 with extensibility. The wings 1330 can be provided with extensibility in any of the directions specified above for the topsheet and backsheet. It is also possible to provide the wings 1330 with extensibility in a direction or amount that differs from that of the topsheet and backsheet by passing the sanitary napkin 1320 through an apparatus that has a different pattern on the portion of the patterned surface that contacts the wings 1330 from the portion of the apparatus that contacts the main body portion of the absorbent article. The portions of the rolls that will be used to provide the wings with extensibility, if mating rolls are used, may also be positioned closer together, or engage to a greater extent, if the wings 1330 do not have as many layers as the main body portion 1322 does.

The methods of the present invention are also used to emboss and/or bond the components of the sanitary napkin together. FIG. 17 shows that the body-facing surface of the sanitary napkin 1320 may be provided with a plurality of embossments in the form of fusion bonds 1340. The fusion bonds 1340 can be formed by providing a plurality of bonding elements on the patterned surface of the apparatus used to form the absorbent core 1328 into particulate material. The bonding elements may optionally be heated if desired. Typically, in order to bond the components together, at least those components that are bonded together will preferably comprise at least some thermoplastic material. In other embodiments, it may be desirable for the patterned surface to be provided with elements that merely emboss the body-facing surface of the sanitary napkin, and do not form fusion bonds between the components thereof.

The methods of the present invention can, thus, be used to form the absorbent core 1328 into particulate material, provide the topsheet 1324 and backsheet 1326 with extensibility, provide the wings or flaps 1330 with extensibility, to emboss and/or bond the components together, and seal the ends of the sanitary napkin 1320. This can all be accomplished in a single pass through an apparatus similar to that shown in the drawings. Further, as shown in FIG. 18, the bonding pattern can penetrate the topsheet all the way to the backsheet to provide the absorbent material with integrity by compartmentalizing the same. For example, the absorbent material can comprise a thermally bonded airlaid material. In such an embodiment, it may not be necessary to provide conventional binder fibers or powder binders to maintain the integrity of the material.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. A method of bonding a laminate, the method comprising the steps of:
   (a) providing an anvil roll and a patterned roll, said anvil roll and said patterned roll being capable of counter-rotating in relation to each other, said anvil roll having an anvil roll surface and said patterned roll having a patterned roll surface, at least one load bearing member disposed between said patterned roll surface and said anvil roll surface, said load bearing member having a caliper, at least one pattern element extending from said patterned roll surface, said pattern element having a height, said caliper of said load bearing member being greater than said height of said pattern element;
   (b) providing a loading force to press said anvil roll to said patterned roll;
   (c) providing a laminate between said patterned roll surface and said anvil roll surface; and
   (d) counter-rotating said anvil roll and said patterned roll in relation to one another to compress said laminate between said pattern element and said anvil roll surface to effect a bond in said laminate.

2. The method of claim 1, wherein said pattern element has a land surface, said land surface is selected from the group consisting of a circle, and an oval.

3. The method of claim 1, wherein said load bearing member is integral with said pattern roll.

4. The method of claim 1, wherein said load bearing member is on said anvil roll.

5. An apparatus for bonding or embossing a laminate, the apparatus comprising: an anvil roll and a patterned roll, said anvil roll and said patterned roll being capable of counter-rotating in relation to each other, said anvil roll having an anvil roll surface and said patterned roll having a patterned roll surface, at least one load bearing member disposed between said patterned roll surface and said anvil roll surface, said load bearing member having a caliper, at least one pattern element extending from said patterned roll surface, said pattern element having a height, said caliper of said load bearing member being greater than said height of said pattern element.

6. The apparatus of claim 5, wherein said pattern element has a land surface, said land surface is selected from the group consisting of a circle, and an oval.

7. The apparatus of claim 5, wherein said load bearing member is integral with said pattern roll.

8. The method of claim 5, wherein said load bearing member is on said anvil roll.

* * * * *